United States Patent
Warren et al.

(10) Patent No.: US 8,453,498 B2
(45) Date of Patent: Jun. 4, 2013

(54) ACTUATABLE CAPACITIVE TRANSDUCER FOR QUANTITATIVE NANOINDENTATION COMBINED WITH TRANSMISSION ELECTRON MICROSCOPY

(75) Inventors: Oden L. Warren, New Brighton, MN (US); Syed Amanula Syed Asif, Bloomington, MN (US); Edward Cyrankowski, Woodbury, MN (US); Kalin Kounev, Shoreview, MN (US)

(73) Assignee: Hysitron, Inc., Minneapolis, MN (US)

( * ) Notice: Subject to any disclaimer, the term of this patent is extended or adjusted under 35 U.S.C. 154(b) by 380 days.

(21) Appl. No.: 12/886,745

(22) Filed: Sep. 21, 2010

(65) Prior Publication Data

US 2011/0005306 A1 Jan. 13, 2011

Related U.S. Application Data

(62) Division of application No. 11/672,489, filed on Feb. 7, 2007, now Pat. No. 7,798,011.

(60) Provisional application No. 60/771,560, filed on Feb. 8, 2006.

(51) Int. Cl.
*G01B 5/28* (2006.01)
*G01B 7/16* (2006.01)
*G01L 1/00* (2006.01)

(52) U.S. Cl.
USPC .............................................. 73/105; 73/780

(58) Field of Classification Search
USPC ........................................................ 73/105
See application file for complete search history.

(56) References Cited

U.S. PATENT DOCUMENTS

| | | | |
|---|---|---|---|
| 4,196,632 A | 4/1980 | Sikorra | |
| 4,498,043 A | 2/1985 | Heathcote et al. | |
| 4,694,687 A | 9/1987 | Bonin et al. | |
| 5,006,952 A | 4/1991 | Thomas | |
| 5,193,383 A * | 3/1993 | Burnham et al. | ............... 73/105 |
| 5,553,486 A | 9/1996 | Bonin | |
| 5,576,483 A | 11/1996 | Bonin | |

(Continued)

FOREIGN PATENT DOCUMENTS

JP 6241780 9/1994

OTHER PUBLICATIONS

Yang, Shuang. "Nanoindentation of Polymer Materials" Thesis for National University of Singapore. 2003. [Online] http://scholarbank.nus.edu.sg/bitstream/handle/10635/13983/YangS.pdf?sequence=1.*

Japanese Office Action, Oct. 18, 2011, 3 pages.

(Continued)

*Primary Examiner* — Lisa Caputo
*Assistant Examiner* — Jonathan Dunlap
(74) *Attorney, Agent, or Firm* — Arlene Hornilla; Steven Dicke; Gregg Kromrey

(57) ABSTRACT

An actuatable capacitive transducer including a transducer body, a first capacitor including a displaceable electrode and electrically configured as an electrostatic actuator, and a second capacitor including a displaceable electrode and electrically configured as a capacitive displacement sensor, wherein the second capacitor comprises a multi-plate capacitor. The actuatable capacitive transducer further includes a coupling shaft configured to mechanically couple the displaceable electrode of the first capacitor to the displaceable electrode of the second capacitor to form a displaceable electrode unit which is displaceable relative to the transducer body, and an electrically-conductive indenter mechanically coupled to the coupling shaft so as to be displaceable in unison with the displaceable electrode unit.

27 Claims, 17 Drawing Sheets

U.S. PATENT DOCUMENTS

| | | | |
|---|---|---|---|
| 5,661,235 A | | 8/1997 | Bonin |
| 5,834,643 A | | 11/1998 | Cheng |
| 5,869,751 A | | 2/1999 | Bonin |
| 6,026,671 A | | 2/2000 | Battenfeld |
| 6,026,677 A | * | 2/2000 | Bonin ............................. 73/105 |
| 7,046,497 B1 | | 5/2006 | Bonin |
| 8,161,803 B2 | * | 4/2012 | Oh et al. ........................... 73/81 |
| 2004/0011119 A1 | | 1/2004 | Jardret et al. |
| 2005/0103996 A1 | * | 5/2005 | Olin et al. ..................... 250/311 |
| 2007/0103697 A1 | * | 5/2007 | Degertekin ................... 356/501 |
| 2008/0276727 A1 | * | 11/2008 | Enoksson et al. .......... 73/862.68 |

OTHER PUBLICATIONS

Yu, High-resolution capacitive load-displacement transducer and its application in nanoindentation and adhesion force measurements, American Institute of Physics, 2005, 8 pages.

Search Report, EP, Jul. 2, 2012, 7 pages.

PCT Search Report, Feb. 12, 2008, 2 pages.

* cited by examiner

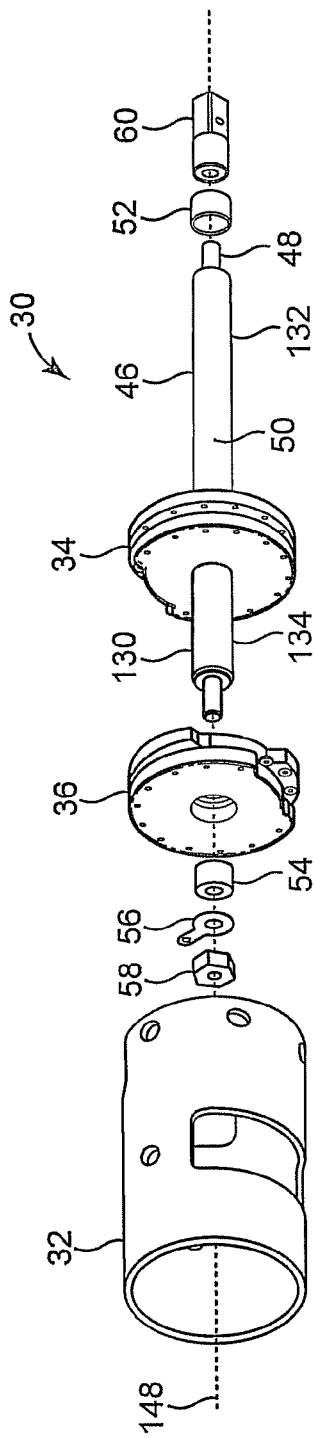
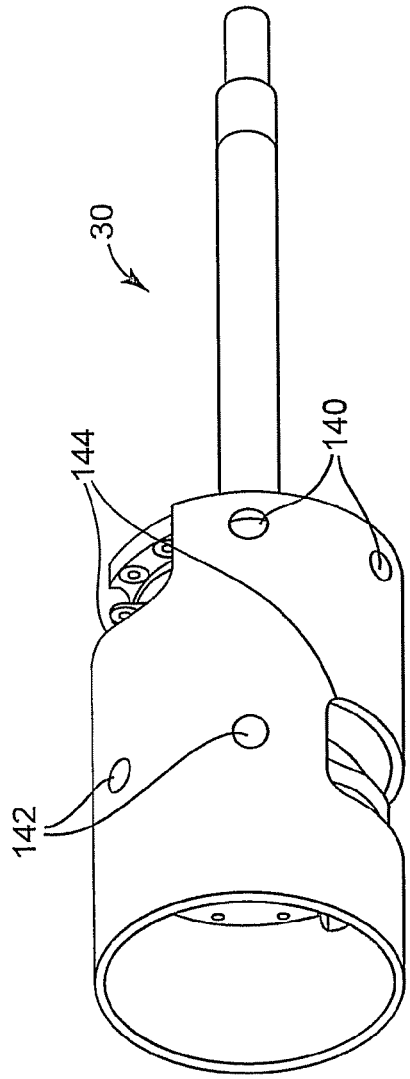
Fig. 5a
Fig. 5b

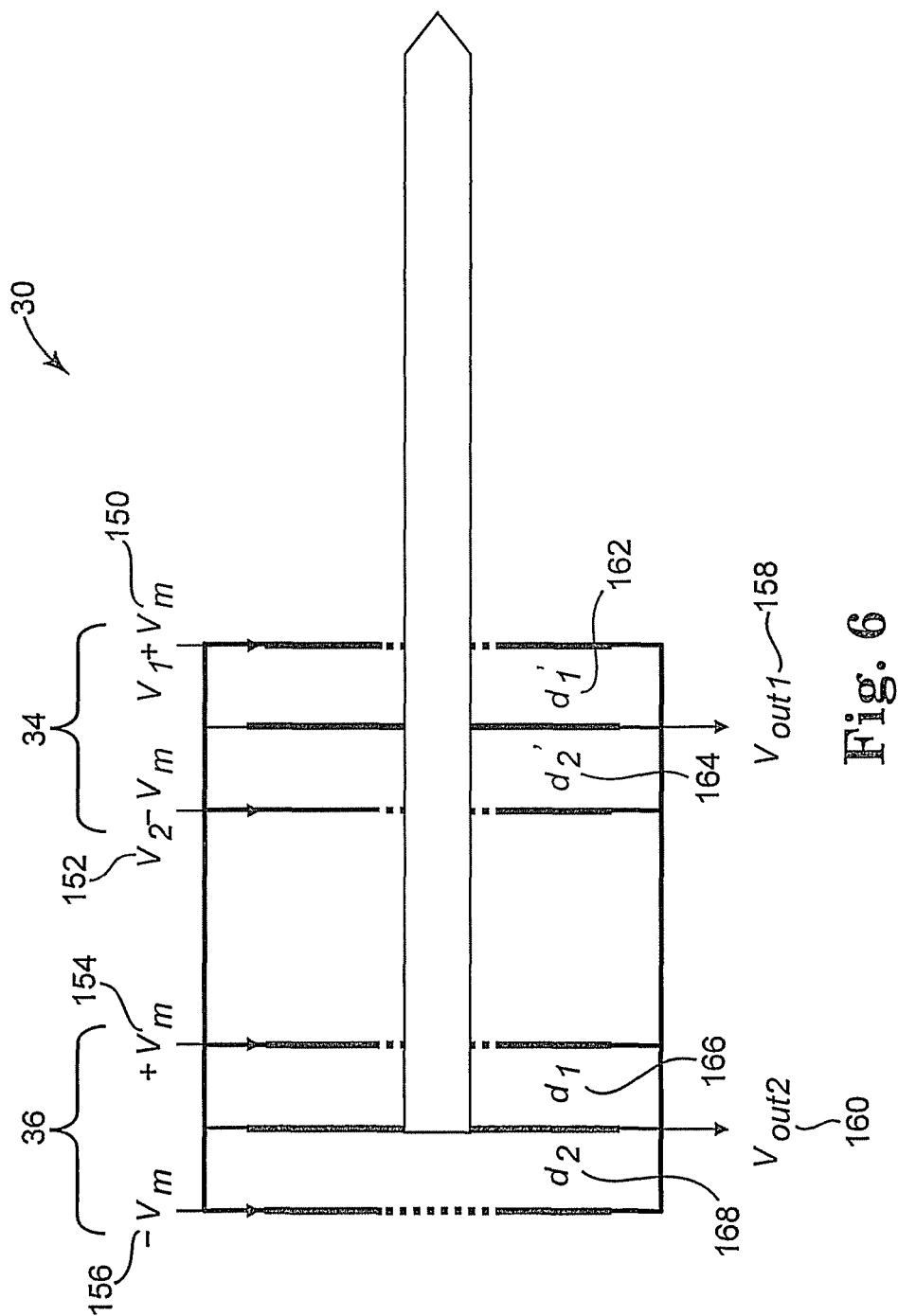

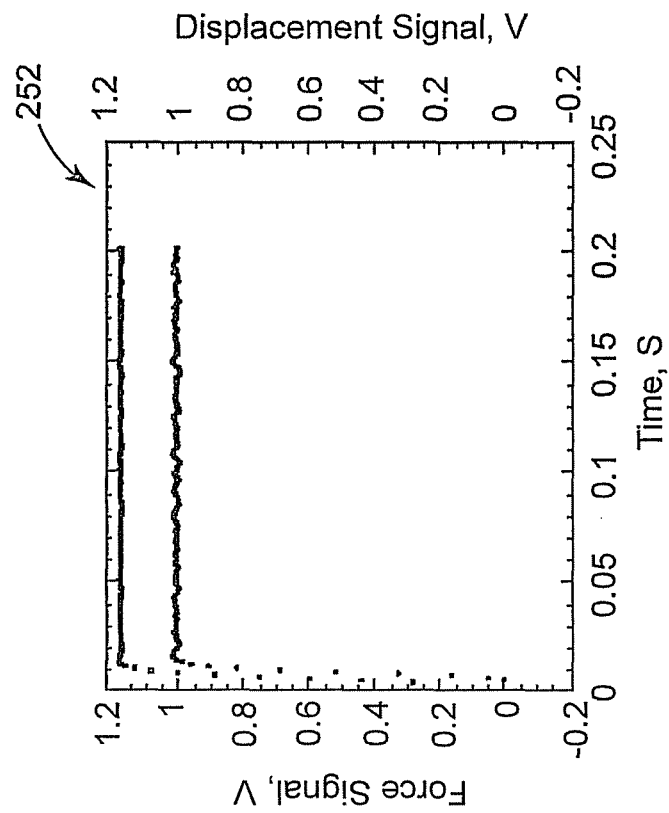
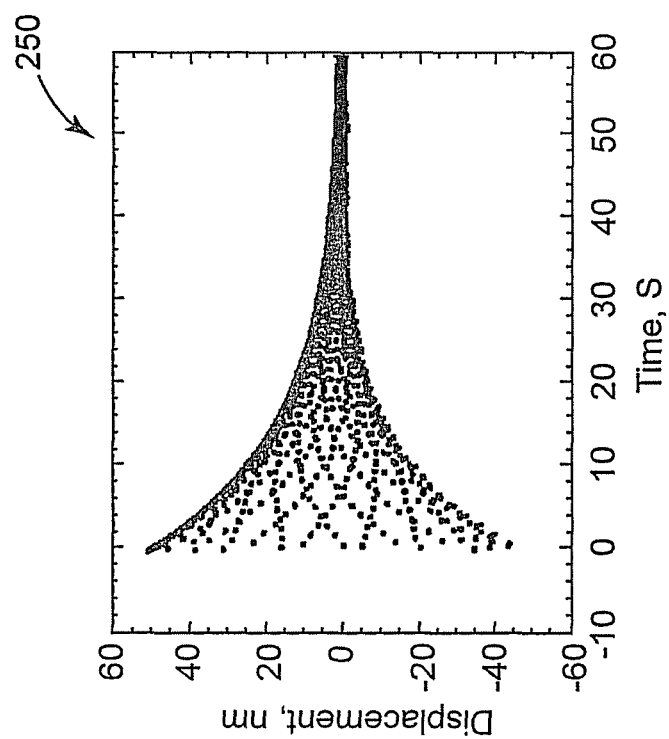
Fig. 10b
Fig. 10a

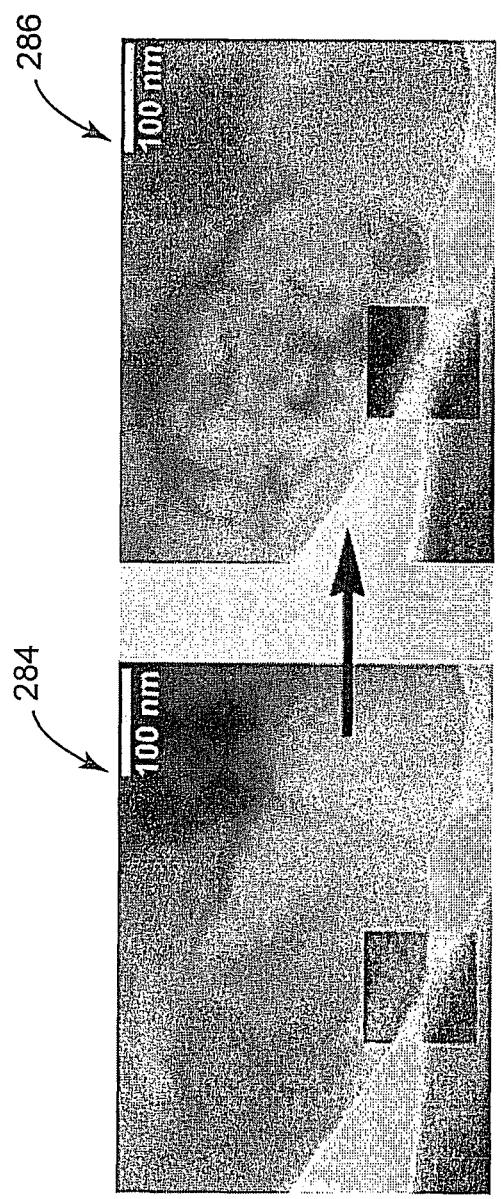

ACTUATABLE CAPACITIVE TRANSDUCER FOR QUANTITATIVE NANOINDENTATION COMBINED WITH TRANSMISSION ELECTRON MICROSCOPY

CROSS-REFERENCE TO RELATED APPLICATION

This Utility patent application is a Divisional application of U.S. patent application Ser. No. 11/672,489, filed Feb. 7, 2007, which claims benefit from U.S. Provisional Patent Application No. 60/771,560, filed Feb. 8, 2006, priority to which is claimed under 35 U.S.C. §119(e) and which are both incorporated herein by reference.

STATEMENT REGARDING FEDERALLY SPONSORED RESEARCH OR DEVELOPMENT

This invention may be related to work done with Government support under Grant No. DE-FG02-04ER83979 awarded by the Department of Energy.

BACKGROUND

Each reference from the following list of references is incorporated herein by reference:
1. A. C. Fischer-Cripps, *Nanoindentation* (Springer, New York, 2004). ("Reference 1")
2. "Review of instrumented indentation", M. R. VanLandingham, *J. Res. Natl. Inst. Stand. Technol.* 108, 249 (2003). ("Reference 2")
3. "An improved technique for determining hardness and elastic modulus using load and displacement sensing indentation measurements", W. C. Oliver and G. M. Pharr, *J. Mater. Res.* 7, 1564 (1992). ("Reference 3")
4. "Challenges and interesting observations associated with feedback-controlled nanoindentation", O. L. Warren, S. A. Downs, and T. J. Wyrobek, *Z. Metallkd.* 95, 287 (2004). ("Reference 4")
5. For a recent review of in-situ TEM techniques: "New developments in transmission electron microscopy for nanotechnology", Z. L. Wang, *Adv. Mater.* 15, 1497 (2003). ("Reference 5")
6. "Development of an in situ nanoindentation specimen holder for the high voltage electron microscope", M. A. Wall and U. Dahmen, *Microsc. Microanal.* 3, 593 (1997). ("Reference 6")
7. "An in situ nanoindentation specimen holder for a high voltage transmission electron microscope", M. A. Wall and U. Dahmen, *Microsc. Res. Tech.* 42, 248 (1998). ("Reference 7")
8. "Development of a nanoindenter for in situ transmission electron microscopy", E. A. Stach, T. Freeman, A. M. Minor, D. K. Owen, J. Cumings, M. A. Wall, T. Chraska, R. Hull, J. W. Morris, Jr., A. Zettl, and U. Dahmen, *Microsc. Microanal.* 7, 507 (2001). ("Reference 8")
9. "Quantitative in situ nanoindentation in an electron microscope", A. M. Minor, J. W. Morris, and E. A. Stach, *Appl. Phys. Lett.* 79, 1625 (2001). ("Reference 9")
10. "In-situ transmission electron microscopy study of the nanoindentation behavior of Al", A. M. Minor, E. T. Lilleodden, E. A. Stach, and J. W. Morris, Jr., *J. Electr. Mater.* 31, 958 (2002). ("Reference 10")
11. "In-situ nanoindentation—a unique probe of deformation response in materials", A. Minor, E. Lilleodden, M. Jin, E. Stach, D. Chrzan, B. Morris, T. Friedmann, X. Xiao, J. Carlisle, and O. Auciello, *Microsc. Microanal.* 9, 900 (2003). ("Reference 11")
12. "An in-situ TEM nanoindenter system with 3-axis inertial positioner", M. S. Bobji, C. S. Ramanujan, R. C. Doole, J. B. Pethica, and B. J. Inkson, *Mater. Res. Soc. Symp. Proc.* 778, U4.5.1 (2003). ("Reference 12")
13. "Direct observations of incipient plasticity during nanoindentation of Al", A. M. Minor, E. T. Lilleodden, E. A. Stach, and J. W. Morris, Jr., *J. Mater. Res.* 19, 178 (2004). ("Reference 13")
14. "Dislocation-grain boundary interactions in martensitic steel observed through in situ nanoindentation in a transmission electron microscope", T. Ohmura, A. M. Minor, E. A. Stach, and J. W. Morris, Jr., *J. Mater. Res.* 19, 3626 (2004). ("Reference 14")
15. "Effects of solute Mg on grain boundary and dislocation dynamics during nanoindentation of Al—Mg thin films", W. A. Soer, J. Th. M. De Hosson, A. M. Minor, J. W. Morris, Jr., and E. A. Stach, *Acta Mater.* 52, 5783 (2004). ("Reference 15")
16. "Study of deformation behavior of ultrafine-grained materials through in situ nanoindentation in a transmission electron microscope", M. Jin, A. M. Minor, D. Ge, and J. W. Morris, Jr., *J. Mater. Res.* 20, 1735 (2005). ("Reference 16")
17. "Room temperature dislocation plasticity in silicon", A. M. Minor, E. T. Lilleodden, M. Jin, E. A. Stach, D. C. Chrzan, and J. W. Morris, Jr., *Philos. Mag.* 85, 323 (2005). ("Reference 17")
18. "Indentation mechanics of Cu—Be quantified by an in situ transmission electron microscopy mechanical probe", M. S. Bobji, J. B. Pethica, and B. J. Inkson, *J. Mater. Res.* 20, 2726 (2005). ("Reference 18")
19. Brochure from Gatan Inc. titled "In situ probing: STM-TEM systems from Nanofactory™ Instruments". ("Reference 19")
20. Presentation from Gatan Inc. titled "TEM-nanoindentor system from Nanofactory", authored by Oleg Lourie, Gatan Inc. ("Reference 20")
21. ISO 14577-1:2002 ("Metallic materials—instrumented indentation test for hardness and materials parameters—part 1: test method"); ISO 14577-2:2002 ("Metallic materials—instrumented indentation test for hardness and materials parameters—part 2: verification and calibration of testing machines"); ISO 14577-3:2002 ("Metallic materials—instrumented indentation test for hardness and materials parameters—part 3: calibration of reference blocks"). ("Reference 21")
22. "Effect of PZT and PMN actuator hysteresis and creep on nanoindentation measurements using force microscopy", S. M. Hues, C. F. Draper, K. P. Lee, and R. J. Colton, *Rev. Sci. Instrum.* 65, 1561 (1994). ("Reference 22")
23. "The effect of instrumental uncertainties on AFM indentation measurements", M. R. VanLandingham, *Microsc. Today* 97, 12 (1997). ("Reference 23")
24. "Quantification issues in the identification of nanoscale regions of homopolymers using modulus measurement via AFM nanoindentation", C. A. Clifford and M. P. Seah, *Appl. Surf. Sci.* 252, 1915 (2005). ("Reference 24")
25. "A micromachined nanoindentation force sensor", A. Nafari, A. Danilov, H. Rödjegård, P. Enoksson, and H. Olin, *Sens. Actuators, A,* 123-124, 44 (2005). ("Reference 25")
26. Brochure from Hysitron, Inc. titled "TriboIndenter®: nanomechanical test instruments"; brochure from Hysitron, Inc. titled "Ubi 1®: scanning quasistatic nanoindentation"; brochure from Hysitron, Inc. titled "TriboScope®: quantitative nanomechanical testing for AFMs". ("Reference 26")

27. "A new force sensor incorporating force-feedback control for interfacial force microscopy", S. A. Joyce and J. E. Houston, *Rev. Sci. Instrum.* 62, 710 (1991). ("Reference 27")

28. "Interfacial force microscopy: a novel scanning probe technique for imaging and quantitative measurement of interfacial forces and nanomechanical properties", O. L. Warren, J. F. Graham, and P. R. Norton, *Phys. Can.* 54, 122 (1998). ("Reference 28")

29. "Apparatus for microindentation hardness testing and surface imaging incorporating a multi-plate capacitor system", W. A. Bonin, U.S. Pat. Nos. 5,553,486 and 6,026,677. ("Reference 29")

30. "Capacitive transducer with electrostatic actuation", W. A. Bonin, U.S. Pat. No. 5,576,483. ("Reference 30")

31. "Multi-dimensional capacitive transducer", W. A. Bonin, U.S. Pat. Nos. 5,661,235 and 5,869,751. ("Reference 31")

32. "Nanoindentation and picoindentation measurements using a capacitive transducer system in atomic force microscopy", B. Bhushan, A. V. Kulkarni, W. Bonin, and J. T. Wyrobek, *Philos. Mag. A* 74, 1117 (1996). ("Reference 32")

33. For example: "Vertical comb-finger capacitive actuation and sensing for CMOS-MEMS", H. Xie and G. K. Fedder, *Sens. Actuators, A* 95, 212 (2002). ("Reference 33")

34. "Force-sensing system, including a magnetically mounted rocking element", J. E. Griffith and G. L. Miller, U.S. Pat. No. 5,307,693. ("Reference 34")

35. "A rocking beam electrostatic balance for the measurement of small forces", G. L. Miller, J. E. Griffith, E. R. Wagner, and D. A. Grigg, *Rev. Sci. Instrum.* 62, 705 (1991). ("Reference 35")

36. "High-resolution capacitive load-displacement transducer and its application in nanoindentation and adhesion measurements", N. Yu, W. A. Bonin, and A. A. Polycarpou, *Rev. Sci. Instrum.* 76, 045109 (2005). ("Reference 36")

37. "Tapping mode imaging with an interfacial force microscope", O. L. Warren, J. F. Graham, and P. R. Norton, *Rev. Sci. Instrum.* 68, 4124 (1997). ("Reference 37")

38. "Nanoindentation and contact stiffness measurement using force modulation with a capacitive load-displacement transducer", S. A. S. Asif, K. J. Wahl, and R. J. Colton, *Rev. Sci. Instrum.* 70, 2408 (1999). ("Reference 38")

39. "Quantitative imaging of nanoscale mechanical properties using hybrid nanoindentation and force modulation", S. A. S. Asif, K. J. Wahl, R. J. Colton, and O. L. Warren, *J. Appl. Phys.* 90, 1192 (2001); *Erratum* 90, 5838 (2001). ("Reference 39")

40. "High-performance drive circuitry for capacitive transducers", W. Bonin, U.S. Pat. No. 6,960,945. ("Reference 40")

Nanoindentation (see References 1 and 2), today's primary technique for probing small volumes of solids for the purpose of quantifying their mechanical properties, involves the use of an instrument referred to as a nanoindenter to conduct a nanoindentation test. At a minimum, a nanoindentation test entails a gradual loading followed by a gradual unloading of a sharp indenter against a sample. The indenter is usually made of diamond, diamond being both the stiffest and the hardest known material. The indenter is shaped to a well-defined geometry typically having an apical radius of curvature in the range of 50-100 nm. The most prevalent indenter geometry is the three-sided pyramidal Berkovich geometry, which imposes a representative strain of ~7% if perfectly formed.

A hallmark of nanoindentation is the acquisition throughout the nanoindentation test of both the force applied to the sample (peak load typically <10 mN) and the indenter displacement into the sample (maximum penetration depth typically <10 µm) to generate a force-displacement curve. High-performance nanoindenters exhibit force and displacement noise floors below 1 µN RMS and 1 nm RMS, respectively. The sample's mechanical properties, such as elastic modulus and hardness, can be evaluated by analyzing the force-displacement curve, the most common method of analysis being the elastic unloading analysis published by Oliver and Pharr (see Reference 3) in 1992.

Nanoindentation suffers from a major shortcoming, however. Despite more than a decade's worth of maturation, nanoindentation still leaves much to be desired in terms of providing definitive mechanistic explanations for certain features of its outputted force-displacement curves. For example, the commonly observed load-controlled nanoindentation phenomenon of a pop-in transient (see Reference 4), a sudden sizeable increase in penetration depth without a corresponding increase in load, an event signaling discontinuous yielding, has many possible interpretations: dislocation burst, shear band formation, fracture onset, spalling, stress-induced phase transformation, etc. Because it is extremely difficult to image such discrete nano-to-atomistic scale happenings at their moments of occurrence, it is not surprising that the scientific literature is replete with examples of deformation mechanisms assigned to pop-in transients with little more to go on than knowledge of the nature of the sample under investigation in combination with educated speculation. The invention provides the opportunity to make unambiguous the microscopic origin of a pop-in transient, or that of any other encountered nanoindentation phenomenon, by coupling nanoindentation to a TEM in an in-situ manner (see Reference 5). Doing so required meeting a set of configurational and environmental challenges not anticipated by existing nanoindentation transducers.

Configurational challenges presented by TEMs include: (1) severely restricted space mandating a nanoindentation transducer considerably more miniature than those currently supplied with commercial nanoindenters; (2) achieving acceptably high maximums in load and penetration depth in spite of the limited size of the transducer; (3) the need to operate the transducer with its indenter horizontal rather than in the standard vertical orientation; (4) the requirement that the indenter extend significantly from the transducer's body to reach well into the TEM's pole piece gap, which necessitates means for countering the associated tilting moment; (5) the requirement that the transducer be largely insensitive with respect to being rotated about the indenter's axis; and (6) the requirement that the transducer achieve high performance in spite of long wiring runs from the transducer residing in vacuum to its electronic circuitry residing out of vacuum, the longer the wiring runs, the greater the likelihood of electromagnetic interference pick-up and capacitive signal loading.

Environmental challenges presented by TEMs include: (1) high vacuum (e.g., $10^{-7}$ torr) limiting construction materials to those not prone to outgassing; (2) the requirement that the transducer not seriously impede the pumping conductance of the TEM holder so that high vacuum can be achieved in a sensible period of time; (3) high vacuum restricting actuation/sensing strategies to those generating minimal heat; (4) high vacuum increasing the transducer's mechanical quality factor (Q) to a value much higher than in air, the higher the quality factor, the longer the impulse-ring-down time; (5) the presence of a highly energetic electron beam (e.g., 300 kV) impinging the indenter, which necessitates means for bleeding charge from the indenter; and (6) the presence of an especially strong magnetic field (e.g., 2 tesla in magnitude) restricting actuation/sensing strategies to those not relying on magnetic principles, and limiting construction materials to those without ferromagnetic content.

Owing to the severe set of challenges to overcome, previous attempts at in-situ TEM nanoindentation (see References 6-20) have been limited to qualitative or semi-quantitative experimentation. Qualitative in-situ TEM nanoindentation refers to viewing/recording a stream of TEM images that show how a sample deforms during the nanoindentation process without having the technology to acquire a corresponding force-displacement curve. The inability to acquire a force-displacement curve renders this experimental approach of low relevance to the invention. Semi-quantitative in-situ TEM nanoindentation also refers to viewing/recording a stream of TEM images that show how a sample deforms during the nanoindentation process, but with the added dimension of acquiring a corresponding force-displacement curve of poor accuracy relative to metrological standards established for nanoindentation, such as those expressed in ISO 14577 (see Reference 21).

Further discussion of semi-quantitative nanoindentation helps to clarify the meaning of quantitative nanoindentation (quantitative nanoindentation is often referred to as depth-sensing indentation). The in-situ TEM nanoindenter manufactured by Nanofactory Instruments AB (TEM-Nanoindentor: SA2000.N (see References 19 and 20)) is a highly relevant example of a semi-quantitative nanoindenter. Nanofactory's instrument is at odds with metrological standards established for nanoindentation on account of the series loading configuration it adopts. The series loading configuration poses a problem because it does not provide a direct measure of penetration depth. Instead, ignoring factors such as load frame compliance and thermally-induced relative position drift, the penetration depth is equal to the motion provided by an actuator minus the deflection associated with a device inferring load. The change in deflection is virtually equal to the change in motion in the limit of high contact stiffness, where "high" means high relative to the spring constant of the deflectable device inferring load. Consequently, it is virtually impossible to resolve changes in penetration depth in the high contact stiffness limit, a limit very easily reached. In contrast, quantitative nanoindenters exhibit constant penetration depth resolution regardless of the value of the contact stiffness.

To further complicate matters, Nanofactory's instrument relies on a piezoelectric actuator to affect the indenter-sample separation, but the instrument does not have a displacement sensor dedicated to measuring the actuator's extension or contraction (see Reference 20). Computing a piezoelectric actuator's extension or contraction from the voltage applied to the actuator has been shown to be unreliable because such actuators exhibit non-linearity, hysteresis, and creep dependent on the history of use (see Reference 22). Sequential analysis of TEM images that show the indenter penetrating the sample seems to be a viable way of directly quantifying the penetration depth in the absence of direct depth sensing. However, our own experience tells us this method is inconvenient and of dubious accuracy. Moreover, the indenter cannot be seen in dark-field TEM images. Operationally, Nanofactory's instrument is reminiscent of an atomic force microscope (AFM) conducting nanoindentation. There is a long history of AFMs delivering faulty force-displacement curves partially on account of the difficulties just mentioned (see References 23 and 24).

In Nanofactory's instrument, the deflectable device inferring load is a miniature two-plate capacitive transducer (see Reference 25) comprising a stationary electrode and a spring-supported displaceable electrode to which the indenter is attached perpendicularly; "stationary" and "displaceable" mean stationary and displaceable with respect to the transducer's body. The displaceable electrode's deflection is determined by monitoring the change in capacitance. Multiplying the displaceable electrode's deflection by the spring constant of the springs supporting the displaceable electrode yields the force acting on the indenter. Curiously, Nanofactory's instrument does not capitalize its potential for electrostatic actuation (see Reference 20), which prevents it from employing a loading configuration other than the inappropriate series loading configuration.

A suite of nanoindenters manufactured by Hysitron, Inc. (see Reference 26) and the interfacial force microscope (IFM) (see References 27 and 28) originating from Sandia National Laboratories are scanning nanoindenters utilizing actuatable capacitive transducers. Both types of instruments are capable of raster scanning the indenter to image a sample's surface in the manner of an AFM. Useful information regarding deformation mechanisms can be obtained from post-test images of the indent's topography, but such images illustrate no more than the residual deformation field.

At the heart of Hysitron's nanoindenters is a patented three-plate capacitive transducer (see References 29-32) comprising two stationary electrodes and a spring-supported displaceable electrode to which the indenter is attached perpendicularly; "stationary" and "displaceable" mean the same as before. The electrodes are components of a three-plate stack, the displaceable electrode being an element of the center plate. Each stationary electrode has a center hole, one center hole passing through the indenter without hindrance and the other center hole with the purpose of equalizing electrode areas. The dual capability of electrostatic actuation and capacitive displacement sensing is a hallmark of Hysitron's three-plate capacitive transducer. Electrostatic actuation in this case refers to generating an electrostatic force between the displaceable electrode and the stationary electrode through which the indenter passes, which deflects the displaceable electrode with respect to the stationary electrodes. Capacitive displacement sensing in this case refers to sensing the deflection using the well-established differential capacitance half-bridge method involving all three electrodes now widely adopted by microelectromechanical systems (MEMS) (see Reference 33).

Hysitron's nanoindenters adopt a parallel loading configuration, meaning contact stiffness in parallel with the spring constant of the support springs. This loading configuration results in the transducer's capacitive displacement sensing output providing a direct measure of penetration depth, again ignoring factors such as load frame compliance and thermally-induced relative position drift. The calculation of contact force involves the applied electrostatic force and the spring force, the spring force being related to the product of the easily-calibrated spring constant of the support springs and the displaceable electrode's deflection.

At the heart of the IFM is a differential-capacitance displacement sensor (see Reference 27) (IFM sensor for brevity) comprised of two co-planar stationary electrodes facing a torsion-bar-supported rotatable electrode; "stationary" and "rotatable" mean stationary and rotatable with respect to the sensor's body. The rotatable electrode together with a pair of torsion bars extending from opposing edges of the rotatable electrode resembles a torsional pendulum. The indenter is attached perpendicularly to the outer face of the rotatable electrode at a position equivalent to one stationary electrode's center. A hallmark of the IFM is its operation as a torque balance. An electrostatic-force-feedback controller is used to servo the indenter-side electrostatic torque to continuously suppress the rotatable electrode from rotating under the influence of the indenter-sample torque; the non-indenter-side electrostatic torque is held constant by the controller. The well-established differential capacitance half-bridge method involving all three electrodes is used to sense the rotational displacement of the rotatable electrode. But the action of the controller continuously nulls the sensor's capacitive displacement sensing output. The rocking beam sensor (see References 34 and 35) originating from Bell Laboratories is similar to the IFM sensor, but is used for critical dimensional metrology rather than for nanoindentation.

IFMs use a piezoelectric actuator to affect the indenter-sample separation. The motion provided by the piezoelectric actuator in combination with the stiffening action of the electrostatic-force-feedback controller permits direct control of penetration depth, once more ignoring factors such as load frame stiffness and thermally-induced relative position drift. IFMs currently do not have a displacement sensor dedicated to measuring the piezoelectric actuator's extension or contraction; nevertheless, IFMs are quantitative nanoindenters from the viewpoint of loading configuration. Solving the relevant torque balance equation yields the contact force. The rotational spring constant of the torsion bars does not enter into the calculation of contact force because the rotatable electrode is suppressed from rotating.

The IFM sensor is currently too large to be housed in a TEM holder; furthermore, the baseline control effort needed to maintain an extended-length indenter in the horizontal orientation will be highly dependent on TEM-holder rotation angle, as will be the maximum load available for nanoindentation. Nevertheless, actuatable capacitive transducers are highly attractive for quantitative in-situ TEM nanoindentation because their operation is not based on magnetic principles, they draw very little electrical current, thus they generate very little heat, and they possess favorable scaling laws for miniaturization.

The Detailed Description of the invention discloses a novel actuatable capacitive transducer in addition to other novel aspects of the invention. Yu et al. made an initial public disclosure on an alternative actuatable capacitive transducer in the on-line version of Reference 36 on Mar. 28, 2005. The Yu et al. alternative actuatable capacitive transducer clearly is not suitable for quantitative in-situ TEM nanoindentation as disclosed.

For these and other reasons there is a need for the present invention.

SUMMARY

One aspect of the present invention relates to an actuatable capacitive transducer which enables quantitative in-situ nanoindentation in a transmission electron microscope (TEM). The quantitative in-situ TEM nanoindentation technique involves indenting a sample to acquire a quantitative force-displacement curve and simultaneously viewing/recording a stream of TEM images that show how the sample deforms while being indented. This simultaneous capability permits, for example, a direct correlation of a specific transient feature of the force-displacement curve to the sample's sudden change in microstructure.

In one embodiment, the present invention provides an actuatable capacitive transducer including a transducer body, a first capacitor including a displaceable electrode and electrically configured as an electrostatic actuator, and a second capacitor including a displaceable electrode and electrically configured as a capacitive displacement sensor, wherein the second capacitor comprises a multi-plate capacitor. The actuatable capacitive transducer further includes a coupling shaft configured to mechanically couple the displaceable electrode of the first capacitor to the displaceable electrode of the second capacitor to form a displaceable electrode unit which is displaceable relative to the transducer body, and an electrically-conductive indenter mechanically coupled to the coupling shaft so as to be displaceable in unison with the displaceable electrode unit.

BRIEF DESCRIPTION OF THE DRAWINGS

FIG. 5 is additional perspectives of the actuatable capacitive transducer depicted in FIG. 1: a) exploded-view drawing; and b) fully-assembled drawing.

FIG. 6 illustrates the major aspects of the electrical configuration of the actuatable capacitive transducer depicted in FIG. 1. Relative dimensions of the actuatable capacitive transducer are improper for the sake of clarity.

FIG. 10 is a built actuatable capacitive transducer's transient response in a JEOL JEM 3010 TEM: a) out-of-contact impulse-ring-down trace for the open-loop mode; including the exponential decay of the trace's envelope; and b) out-of-contact step-response trace while using the displacement control mode.

DETAILED DESCRIPTION

In the following Detailed Description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

An actuatable capacitive transducer suitable for quantitative in-situ TEM nanoindentation is one novel aspect of the invention. A detailed description of one or more embodiments of an actuatable capacitive transducer according to the present invention follows.

Figure 1:
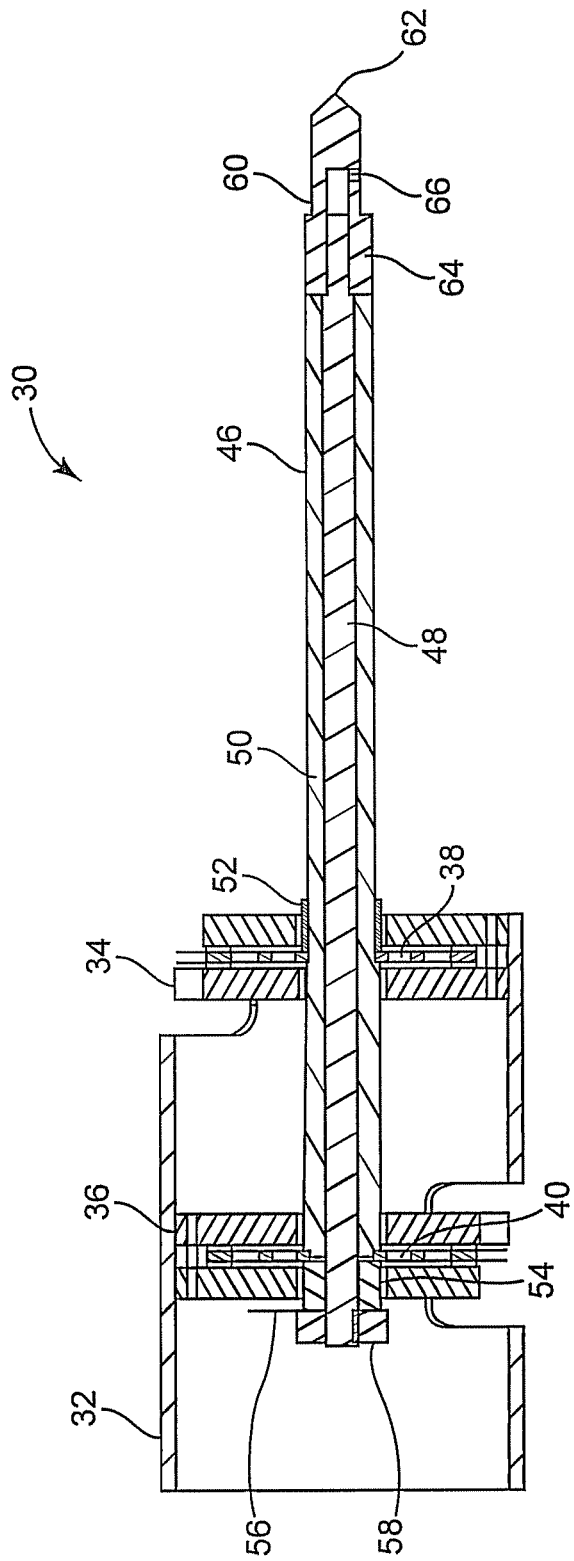
FIG. 1 is a cross-sectional drawing of one embodiment of an actuatable capacitive transducer of the invention.

FIG. 1 is a cross-sectional drawing of one embodiment of an actuatable capacitive transducer 30 according to the present invention. Actuatable capacitive transducer 30 includes an electrically conductive transducer body 32, a first multi-plate capacitor 34, a second multi-plate capacitor 36, and a coupling shaft 46. First and second multi-plate capacitors 34 and 36 are attached to conductive transducer body 32, without electrically shorting them to conductive transducer body 32, such that they are maintained at a fixed separation and are substantially parallel to each other. In one embodiment, conductive transducer body 32 is made of titanium.

As will be described in greater detail below with respect to FIG. 1 and FIG. 2, first and second multi-plate capacitors 34 and 36 respectively include center plates 38 and 40, and each include a displaceable electrode 42 supported from a frame 43 by springs 44, where "displaceable" means displaceable relative to conductive transducer body 32. Coupling shaft 46, as will be described in greater detail below with respect to FIG. 1 and FIG. 2, mechanically couples the displaceable electrodes 42 to form a mechanically-coupled displaceable electrode unit, wherein the mechanically-coupled displaceable electrode unit is displaceable as one unit relative to conductive transducer body 32. In one embodiment, coupling shaft 46 comprises an electrically conductive threaded rod 48 encased, except at its two ends, by a tightly adhered dielectric (electrically insulating) sheath 50. Dielectric sheath 50 is mechanically stiff in order to suppress conductive threaded rod 48, which has a high ratio of length to diameter, from flexing under the influence of a force. Dielectric sheath 50 also electrically insulates conductive threaded rod 48 from the displaceable electrodes 42. In one embodiment, conductive threaded rod 48 is made of brass and dielectric sheath 50 is made of Macor®, a machinable ceramic.

In one embodiment, as illustrated by FIG. 1, actuatable capacitive transducer 30 further includes a dielectric sleeve 52, a dielectric standoff 54, a probe wire tab 56, and an electrically conductive nut 58. Dielectric sleeve 52 reinforces the connection of coupling shaft 46 to the displaceable electrode 42 of first multi-plate capacitor 34. Dielectric standoff 54 reinforces the connection of coupling shaft 46 to the displaceable electrode 42 of second multi-plate capacitor 36 and serves as a base for probe wire tab 56. Probe wire tab 56 slips over an unsheathed end of conductive threaded rod 48 which is located internally to conductive transducer body 32 and is retained against dielectric standoff 54 by screwing on conductive nut 58, such that probe wire tab 56 is in intimate electrical contact with conductive threaded rod 48. In one embodiment, dielectric sleeve 52 and dielectric standoff 54 are each made of Macor®, probe wire tab 56 is made of beryllium copper, and conductive nut 58 is made of brass.

In one embodiment, as illustrated by FIG. 1, actuatable capacitive transducer 30 includes an electrically conductive probe 60. In one embodiment, conductive probe 60 includes an electrically conductive indenter 62 which is mechanically and electrically coupled to an electrically conductive shank 64. Conductive shank 64 is tapped to mate with conductive threaded rod 48 and includes a vent hole 66 to prevent a virtual leak in the high-vacuum environment of a TEM. A portion of conductive shank 64 is square in cross-section (see FIG. 5a) for insertion into a probe mounting tool designed similarly to a nut driver. In one embodiment, conductive probe 60 is screwed onto an unsheathed end of conductive threaded rod 48 which is located externally to conductive transducer body 32, such that conductive probe 60 is in intimate electrical contact with conductive threaded rod 48. It is noted that the ability to screw conductive probe 60 on and off conductive threaded rod 48 facilitates probe storage or probe exchange whenever necessary. In one embodiment, conductive shank 64 is made of titanium and conductive indenter 62 is made of diamond highly through doped with boron and ground to a well-defined geometry, such as the Berkovich geometry, for example. A standard method of attaching a diamond indenter to a titanium shank involves vacuum brazing.

Figure 2:
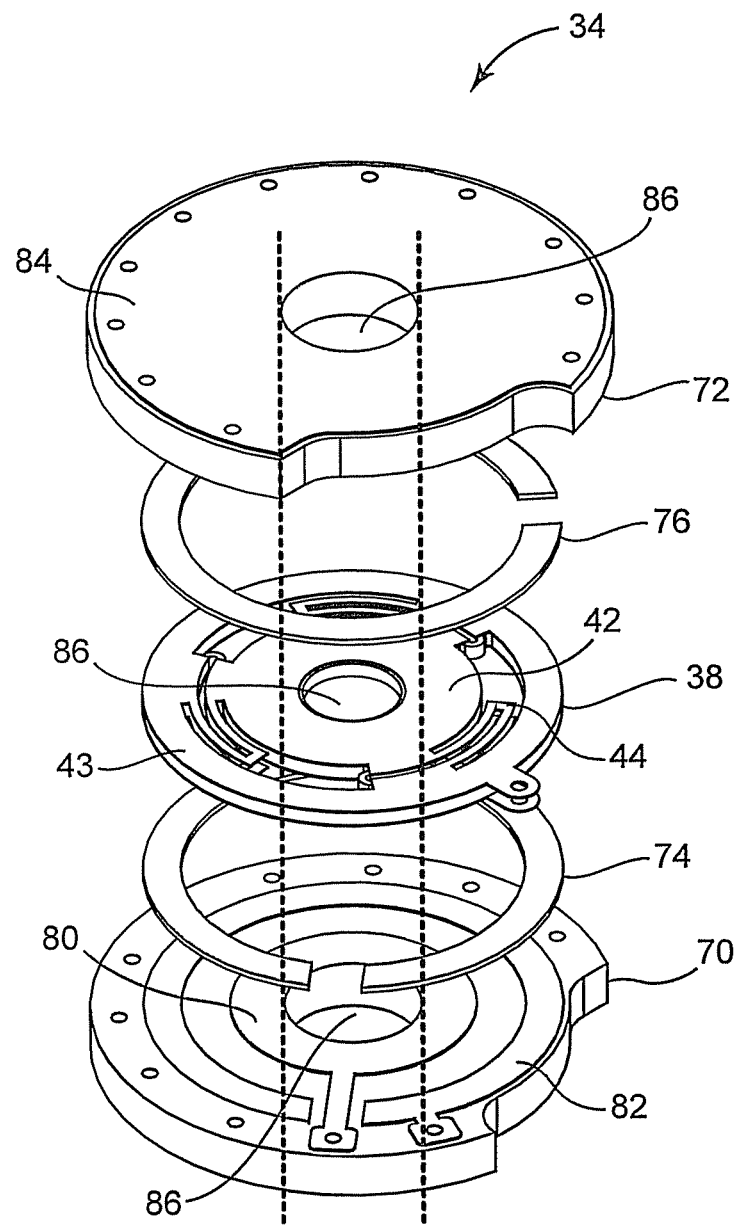
FIG. 2 is an exploded-view drawing of a multi-plate capacitor of the actuatable capacitive transducer depicted in FIG. 1.

FIG. 2 is an exploded-view drawing of one embodiment of a multi-plate capacitor according to the present invention, such as first multi-plate capacitor 34 of FIG. 1. It is noted that the illustration of FIG. 2 and the following description also applies to second multi-plate capacitor 36. In addition to center plate 38, first multi-plate capacitor 34 includes a first outer plate 70, a second outer plate 72, which is substantially identical to first outer plate 70, a first dielectric spacer 74, and a second dielectric spacer 76, which is substantially identical to first dielectric spacer 74. In one embodiment, first and second outer plates 70 and 72 each comprise a dielectric slab having a stationary electrode 80 in the shape of a ring patterned onto one face of the dielectric slab, a guard ring 82 patterned around stationary electrode 80, and a ground plane 84 patterned onto the opposite face of the dielectric slab. The term "stationary", with regard to stationary electrode 80, means stationary relative to the conductive transducer body 32. In one embodiment, first and second outer plates 70 and 72 are made of TMM® 4 patterned with electro-deposited copper cladding, TMM® 4 being a ceramic/polytrifluoroethylene laminate often used in outer space applications, and first and second dielectric spacers 74 and 76 are made of aluminum heavily anodized to achieve electrically insulating surfaces.

First and second outer plates 70 and 72, and center plate 38 each include a center hole 86. In one embodiment, center hole 86 of center plate 38 is smaller in diameter than center holes 86 of first and second outer plates 70 and 72, as indicated by the pair of vertical dashed lines in FIG. 2.

Multi-plate capacitor 34 is constructed as a stack in the order of first outer plate 70, first dielectric spacer 74, center plate 38, second dielectric spacer 76, and second outer plate 72. Again, it is noted that the following description applies to both first and second multi-plate capacitors 34 and 36. Stationary electrode 80 of first outer plate 70 faces one face of displaceable electrode 42 of center plate 38. Stationary electrode 80 (not shown in FIG. 2) of second outer plate 72 faces the opposite face of displaceable electrode 42 of center plate 38. First dielectric spacer 74 separates and electrically insulates first outer plate 70 from center plate 38. Second dielectric spacer 76 separates and electrically insulates second outer plate 72 from center plate 38. The thickness of first dielectric spacer 74 is a dominant factor in determining a first electrode gap, corresponding to the separation between stationary electrode 80 of first outer plate 70 and displaceable electrode 42, and the thickness of second dielectric spacer 76 is a dominant factor in determining a second electrode gap, corresponding to the separation between stationary electrode 80 of second outer plate 72 and displaceable electrode 42.

From a mechanical design viewpoint, first and second multi-plate capacitors 34 and 36 may differ with respect to the thickness of dielectric spacers 74 and 76. In one embodiment, dielectric spacers 74 and 76 of the first multi-plate capacitor 34 each have a thickness of 100 µm, and dielectric spacers 74 and 76 of second multi-plate capacitor 36 each have a thickness of 75 µm. In this embodiment, the difference in thickness between dielectric spacers 74 and 76 of first and second multi-plate capacitors 34 and 36 is related to first multi-plate capacitor 34 functioning primarily as an electrostatic actuator (and secondarily as a capacitive displacement sensor), and second multi-plate capacitor 36 functioning as a capacitive displacement sensor. It is noted that in some instances, first multi-plate capacitor 34 is referred to as the "electrostatic actuator", and second multi-plate capacitor 36 is referred to as the "capacitive displacement sensor", keeping in mind that the electrostatic actuator also functions as an additional capacitive displacement sensor in some embodiments.

Figure 3:
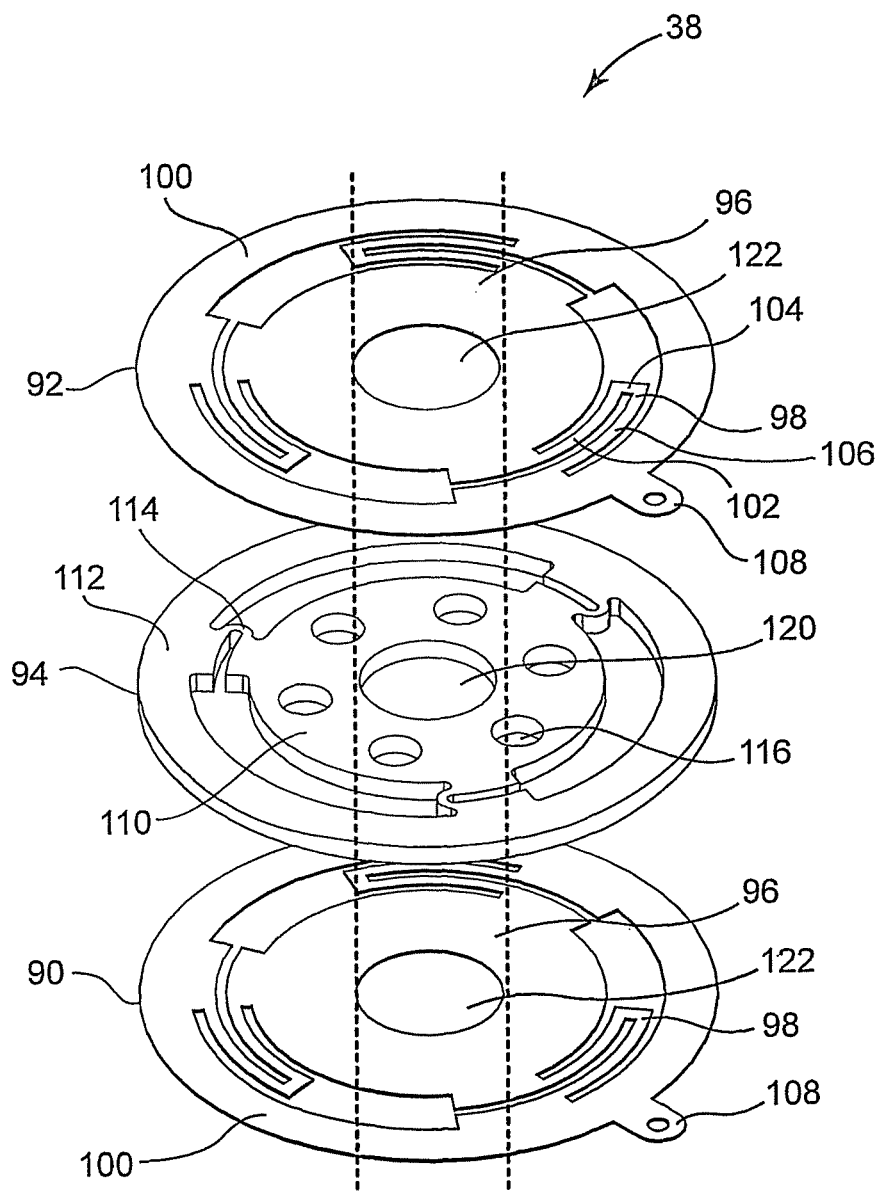
FIG. 3 is an exploded-view drawing of the center plate of a multi-plate capacitor of the actuatable capacitive transducer depicted in FIG. 1.

FIG. 3 is an exploded-view drawing illustrating one embodiment of a center plate of a multi-plate capacitor according to the present invention, such as center plate 38 of first multi-plate capacitor 34. It is noted that the illustration of FIG. 3 and the following description also applies to center plate 40 of second multi-plate capacitor 36. In one embodiment, center plate 38 includes a first spring sheet 90, a second spring sheet 92, which is substantially identical to first spring sheet 90, and a stabilizer 94. In one embodiment, first and second spring sheets 90 and 92 each have an inner ring 96 supported by a set of three substantially identical and equally spaced springs 98 which are coupled to an outer ring 100. In one embodiment, each spring 98 includes an arc shaped first leg 102 following the circumference of inner ring 96, a turning segment 104, and an arc shaped second leg 106 following the circumference of outer ring 100, with arc shaped first and second legs 102 and 106 being adjacent to one another. It is noted that together, springs 98 of first and second spring sheets 90 and 92 are represented as springs 44 in FIG. 2. First and second spring sheets 90 and 92 also include a displaceable-electrode wire tab 108 extending from outer ring 100. In one embodiment, first and second spring sheets 90 and 92, and stabilizer 94 are made of beryllium copper.

In one embodiment, stabilizer 94 includes an inner ring 110 which is initially connected to an outer ring 112 by a set of three substantially identical and equally spaced temporary connectors 114. In one embodiment, inner ring 110 of stabilizer 94 includes a set of six substantially identical and equally spaced weight-reduction holes 116. Initially, as indicated by the vertical dashed lines in FIG. 3, an inside diameter 120 of inner ring 110 of stabilizer 94 is smaller than inside diameters 122 of inner rings 96 of first and second spring sheets 90 and 92. Ultimately, the inside diameters 122 of inner rings 96 of first and second spring sheets 90 and 92 and inside diameter 120 of inner ring 110 of stabilizer 94 are enlarged and form a uniform final diameter for center hole 86 of center plate 38, as illustrated in FIG. 2.

Center plate 38 is constructed as a stack in the order of first spring sheet 90, stabilizer 94, and second spring sheet 92. In one embodiment, inner rings 96 of first and second spring sheets 90 and 92 and inner ring 110 of stabilizer 94 are laminated together to form displaceable electrode 42. Similarly, outer rings 100 of first and second spring sheets 90 and 92 and outer ring 112 of stabilizer 94 are laminated together to form frame 43. It is noted that springs 98 of first and second spring sheets 90 and 92 must be kept free of adhesive and form springs 44. Displaceable-electrode wire tabs 108 of first and second spring sheets 90 and 92 are wired together to ensure that first and second spring sheets 90 and 92 are at the same electrical potential. In one embodiment, as a precaution against introducing a virtual leak in the high-vacuum environment of a TEM, weight-reduction holes 116 of stabilizer 94 are filled with adhesive during the process of constructing center plate 38.

In some instances, construction of center plate 38, as described above, results in a non-concentric alignment of the inside diameters 122 of inner rings 96 of first and second spring sheets 90 and 92 and inside diameter 120 of stabilizer 94. In one embodiment, using the smaller inside diameter 120 of inner ring 110 of stabilizer 94 as a pilot hole, inside diameters 122 of inner rings 96 of first and second spring sheets 90 and 92 and inner diameter 120 of stabilizer 94 are enlarged by drilling to establish a substantially uniform final diameter of center hole 86 of center plate 38. After completing the drilling operation, temporary connectors 114 are removed which frees displaceable electrode 42 to move as one unit relative to frame 43 when influenced by a force. The multilayer design of the center plate 38 enables springs 44 to have a low spring constant simultaneous with displaceable electrode 42 having high flexural rigidity.

In one embodiment, the spring constant of springs 44 is optimized relative to the flexural rigidity of displaceable electrode 42. In one embodiment, the spring constant of springs 44 was optimized with the aid of modeling by finite-element analysis (FEA). In one embodiment, the finalized design of springs 44 resulted in a nominal modeled spring constant of 197N/m for actuatable capacitive transducer 30 (each of twelve springs contributing 16.4N/m). Taking into account dimensional tolerances, spring constant k of actuatable capacitive transducer 30 is predicted to fall in the range of 111-345N/m, primarily as a consequence of a strong dependence on an uncertainty in a thickness t of the first and second spring sheets 90 and 92 ($k \propto t^3$). In one embodiment, actuatable capacitive transducer 30 was determined to have a measured k of 259N/m, somewhat higher than a nominal modeled k of 197N/m, but within a range of possible values. It is noted that the nominal modeled k is approximately the same as that of Hysitron's three-plate capacitive transducer, which is comprised of a single three-plate capacitor of square shape having a total of eight springs of different shape and dimensions in comparison to springs 44 of actuatable capacitive transducer 30.

In one embodiment, FEA was used further to predict whether springs 44 obeyed Hooke's law when displaceable electrode 42 was forced to displace up to 5 µm from its natural state in a manner that only caused a uniform change in the electrode gaps, wherein "natural state" refers to a positional state of displaceable electrode 42 when not under the influence of electrostatic and indenter-sample forces. The FEA results predict excellent adherence to Hooke's law over this range of displacement, a range easily large enough for quantitative in-situ TEM nanoindentation because the depth of electron transparency in a sample is only in the vicinity of 300 nm for a 300 kV electron beam. FEA was used further still to predict the largest local strain induced in springs 44 when displaceable electrode 42 was forced to displace 75 μm from its natural state in the manner described above. This amount of displacement is equivalent to displaceable electrode 42 of the more narrowly gapped second multi-plate capacitor 36, in one embodiment, being forced to contact a neighboring stationary electrode. At 75 μm displacement, the largest local strain in springs 44 is predicted to be 0.08%, well under the expected elastic strain limit of 0.2%.

Returning to FIG. 2, multi-plate capacitor 34 is formed by adhering first dielectric spacer 74 both to first outer plate 70 and frame 43 of center plate 38, and by adhering second dielectric spacer 76 both to second outer plate 72 and frame 43 of center plate 38. Springs 44 and displaceable electrode 42 must be kept free of adhesive during the joining procedure.

Figure 4B:
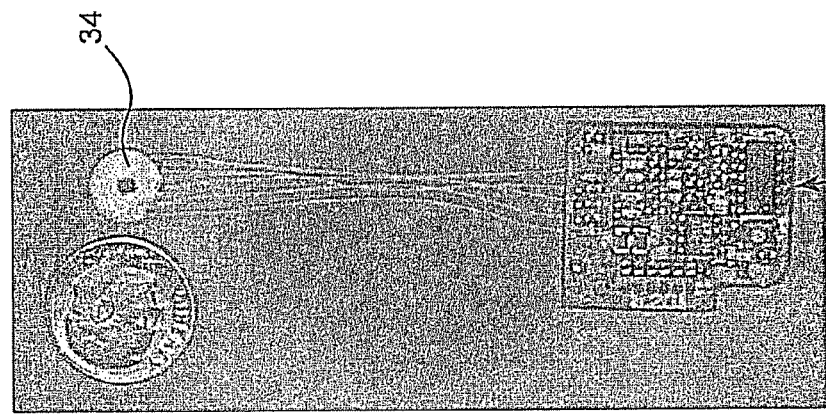
FIG. 4 is a multi-plate capacitor of the actuatable capacitive transducer depicted in FIG. 1: a) fully-assembled drawing; and b) photograph of a built multi-plate capacitor showing its size relative to a US dime.
Figure 4A:
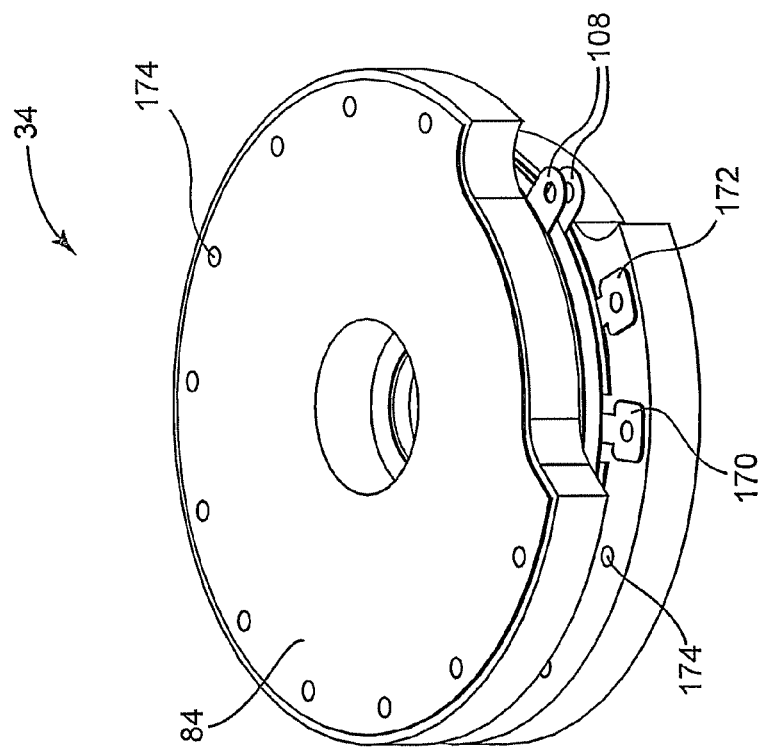

FIG. 4A is a perspective view representative of one embodiment of multi-plate capacitor 34 in an assembled condition. As can be seen in FIG. 4B, assembled multi-plate capacitor 34 is substantially smaller than a U.S. dime.

FIG. 5A is an exploded-view drawing further illustrating actuatable capacitive transducer 30 described by FIGS. 1 through 4A above. FIG. 5B is a perspective view drawing illustrating actuatable capacitive transducer 30 in an assembled condition. With respect to FIG. 5A, dielectric sheath 50 of coupling shaft 46 has a segment 130 of a major diameter and first and second segments 132 and 134 of a minor diameter, with minor-diameter segment 132 being longer than minor-diameter segment 134. The minor diameter of first and second segment 132 and 134 is a tight fit to the drilled-out uniform final diameter of center holes 86 of center plates 38 and 40 of first and second multi-plate capacitors 34 and 36. The major diameter of segment 130 is larger than the minor diameter of first and second segments 132 and 134, but is small enough in comparison to the diameter of center holes 86 of first and second outer plates 70 and 72 of first and second multi-plate capacitors 34 and 36 to prevent coupling shaft 46 from contacting the relevant outer plates after assembly of actuatable capacitive transducer 30.

With reference to FIG. 5A, the following describes an example of a sequence of steps for assembling actuatable capacitive transducer 30. First, pre-assembled first multi-plate capacitor 34 is slipped over longer minor-diameter segment 132 of dielectric sheath 50, which is pre-adhered to conductive threaded rod 48. Displaceable electrode 42 of first multi-plate capacitor 34 is then adhered against a shoulder defined by the transition from longer minor-diameter segment 132 to major-diameter segment 130 of dielectric sheath 50. Next, dielectric sleeve 52 is slipped over longer minor-diameter segment 132 of dielectric sheath 50. Dielectric sleeve 52 is then adhered to displaceable electrode 42 of first multi-plate capacitor 34 and to dielectric sheath 50, such that dielectric sleeve 52 does not contact the outer plate through which it passes. Next, pre-assembled second multi-plate capacitor 36 is slipped over shorter minor-diameter segment 134 of dielectric sheath 50. Displaceable electrode 42 of second multi-plate capacitor 36 is then adhered against a shoulder defined by the transition from shorter minor-diameter segment 134 to major-diameter segment 130 of dielectric sheath 50. Next, dielectric standoff 54 is slipped over the unsheathed end of conductive threaded rod 48 now protruding from second multi-plate capacitor 36. Dielectric standoff 54 is then adhered to conductive threaded rod 48 and to displaceable electrode 42 of second multi-plate capacitor 36, such that dielectric standoff 54 does not contact the outer plate through which it passes. Next, probe wire tab 56 is slipped over the unsheathed end of conductive threaded rod 48 now protruding from dielectric standoff 54, and is retained by screwing on conductive nut 58. Screwing conductive probe 60 onto the remaining unsheathed end of conductive threaded rod 48 is delayed until just prior to use in order to diminish the likelihood of inadvertently damaging conductive indenter 62.

With reference to FIG. 5B, conductive transducer body 32 has a first set of ports 140 and a second set of ports 142 to facilitate attaching the now mechanically-coupled first and second multi-plate capacitors 34 and 36 to conductive transducer body 32. It is noted that not all ports of first and second sets of ports 140 and 142 are visible in the illustration of FIG. 5B. Conductive transducer body 32 also includes cutouts 144 which will be described in greater detail below.

Continuing with the example sequence of steps for assembling actuatable capacitive transducer 30 described above, the now mechanically-coupled first and second multi-plate capacitors 34 and 36 are inserted into conductive transducer body 32 such that first multi-plate capacitor 34 is aligned with first set of ports 140 and second multi-plate capacitor 36 is approximately aligned with second set of ports 142. Next, adhesive is injected into first set of ports 140 to fix first multi-plate capacitor 34 to conductive transducer body 32.

Optimum attachment of second multi-plate capacitor 36 to conductive transducer body 32 requires finely manipulating the position of second multi-plate capacitor 36 until each or a specific one of the displaceable electrodes 42 of first and second multi-plate capacitors 34 and 36 resides, as close as possible, midway between the corresponding flanking stationary electrodes 80 (see FIG. 2). After achieving the desired condition, adhesive is injected into second set of ports 142 to fix second multi-plate capacitor 36 to conductive transducer body 32. In one embodiment, the method used to maintain the desired distance between first and second multi-plate capacitors 34 and 36 during adhesive curing resulted in only a 90 nm deviation from perfectly balancing the gaps of first multi-plate capacitor 34 (the electrostatic actuator). One particular nanoindentation operating mode requires electrostatic actuator 34 having well-balanced electrode gaps.

Properly fixing the position of second multi-plate capacitor 36 requires this assembly step be done with coupling shaft 46 horizontal in order to match the eventual orientation of actuatable capacitive transducer 30 in a TEM. If this assembly step is done with coupling shaft 46 aligned with gravity for example, displaceable electrodes 42 of first and second multi-plate capacitors 34 and 36 would end up far from midway between the flanking stationary electrodes 80 upon reorienting actuatable capacitive transducer 30 for insertion into a TEM.

In one embodiment, as can be seen in FIG. 5A, actuatable capacitive transducer 30 has a central axis 148 about which its components are predominantly circular in shape, and about which its components are predominantly concentric. The choice of circular shapes, rather than square shapes for example, is motivated by actuatable capacitive transducer 30 being configured to be housed in a TEM holder. TEM holders, sometimes referred to as TEM rods, typically posses a tubular geometry. By choosing circular shapes, the electrode areas can be maximized. Also regarding electrode areas, displaceable electrodes 42 have a smaller inside diameter and a larger outside diameter in comparison to stationary electrodes 80. This intentional mismatch in diameters suppresses a change in overlapping electrode area in the event displaceable electrodes 42 are forced to shift sideways with respect to the stationary electrodes 80.

As described above, actuatable capacitive transducer 30 must be oriented with coupling shaft 46 horizontal when operating in a TEM. A horizontal orientation enables conductive indenter 62 to intersect the vertically-aligned electron beam of a TEM. As a consequence of this horizontal orientation, conductive probe 60 will tilt substantially downward if the tilting moment owing to gravity acting on the mass from conductive indenter 62 to displaceable electrode 42 of first multi-plate capacitor 34 is not countered by some means. In addition, conductive indenter 62 contacting a sample having its surface slanted relative to central axis 148 of actuatable capacitive transducer 30 will cause a net sideways force, thereby introducing an additional tilting moment. On account of TEM design, the distance from conductive indenter 62 to displaceable electrode 42 of first multi-plate capacitor 34 cannot be significantly shortened to substantially reduce these tilting moments.

Countering tilting moments is a major impetus for employing second multi-plate capacitor 36. By separating the first and second multi-plate capacitors 34 and 36 by a significant fraction of the distance from conductive indenter 62 to displaceable electrode 42 of first multi-plate capacitor 34, the tendency to tilt is greatly reduced. However, there is a compromise between lengthening the portion of coupling shaft 46 between displaceable electrodes 42 of the first and second multi-plate capacitors 34 and 36 and preserving a high mechanical natural frequency, because the mass of coupling shaft 46 is the dominant mass carried by the springs 44.

The following Expression E.1 can be used to calculate the mechanical natural frequency $v_o$ of a spring-mass system:

$$v_o = \frac{1}{2\pi}\sqrt{\frac{k}{m}}; \quad \text{E.1}$$

where k retains the meaning defined above and m is the sprung mass of actuatable capacitive transducer 30. In one embodiment of actuatable capacitive transducer 30, $v_o$ was measured to be 133 Hz with conductive probe 60 attached, which yielded 372 mg for m given the measured k of 259N/m. The measured $v_o$ of actuatable capacitive transducer 30 is comparable to what generally is found for Hysitron's three-plate capacitive transducer equipped with its probe, which is not electrically conductive.

FIG. 6 is a diagram illustrating aspects of the electrical configuration of actuatable capacitive transducer 30. As illustrated by FIG. 6, the electrostatic actuator (i.e., first multi-plate capacitor 34) has a different electrical configuration compared to the capacitive displacement sensor (i.e., second multi-plate capacitor 36). Signals inputted to electrostatic actuator 34 include $V_1+V_m$, as indicated at 150, to the one of stationary electrodes 80 of electrostatic actuator 34 closest to conductive indenter 62, and $V_2-V_m$, as indicated at 152, to the other stationary electrode 80 of the electrostatic actuator 34. Signals inputted to the capacitive displacement sensor include $+V_m$ to the capacitive displacement sensor's stationary electrode closest to the conductive indenter and $-V_m$ to the other stationary electrode of the capacitive displacement sensor.

Input signals $V_1$ and $V_2$ are electrostatic actuation voltages, while input signals $+V_m$ and $-V_m$, indicated at 154 and 156, are high-frequency modulation voltages equal in frequency, waveform, and amplitude but different in phase by 180°. The frequency of $+V_m$ and $-V_m$ is much higher than $v_o$; therefore, actuatable capacitive transducer 30 does not mechanically respond to these input signals. In one embodiment of a built actuatable capacitive transducer 30, both $+V_m$ and $-V_m$ are 130 kHz square waves with an amplitude of 10V peak-to-peak, and both $V_1$ and $V_2$ cover the range of 0-600V. Displaceable electrode 42 of electrostatic actuator 34 is effectively at ground relative to $V_1$ and $V_2$.

Electrostatic actuator 34 outputs a $V_{out1}$ signal, as indicated at 158, from corresponding displaceable electrode 42. Capacitive displacement sensor 36 outputs a $V_{out2}$ signal, as indicated at 160, from corresponding displaceable electrode 42. The frequency and the waveform of $+V_m$ and $-V_m$ dictate the frequency and the waveform of $V_{out1}$ 158 and $V_{out2}$ 160. In a fashion similar to Hysitron's three-plate capacitive transducer and to the IFM sensor, both electrostatic actuator 34 and capacitive displacement sensor 36 are electrically configured to execute the well-established differential capacitance half-bridge method of displacement detection.

With the differential capacitance half-bridge method, an output signal $V_{out}$ of an appropriately configured multi-plate capacitor (specifically an appropriately configured three-plate capacitor) is ideally given by the following Expression E.2:

$$v_{out} = \frac{C_1 - C_2}{C_1 + C_2}|V_m|; \quad \text{E.2}$$

where $C_1$ is the capacitance between displaceable electrode 42 and one neighboring stationary electrode 80, $C_2$ is the capacitance between displaceable electrode 42 and the other neighboring stationary electrode 80, and $|V_m|$ is the amplitude of either $+V_m$ or $-V_m$. Output signal $V_{out}$ can be of either sign depending on which of $C_1$ and $C_2$ is larger. The amplitude of $V_{out}$ is zero when $C_1=C_2$, and is $|V_m|$ when displaceable electrode 42 is in contact with either neighboring stationary electrode 80. Expression E.2 applies both to $V_{out1}$ and $V_{out2}$. The differential capacitance half-bridge method has the characteristic of being relatively insensitive to tilting of displaceable electrodes 42 relative to stationary electrodes 80 and, thus, to vibrations that induce oscillatory tilting. This is particularly important, because actuatable capacitive transducer 30 is most susceptible to vibrations that induce oscillatory tilting on account of its horizontal orientation in a TEM.

In terms of geometric parameters, the capacitance C of a parallel-plate capacitor is given by Expression E.3 below:

$$C = \frac{\varepsilon_o A}{d}; \quad \text{E.3}$$

where $\varepsilon_o$ is the electrical permittivity constant ($8.85\times10^{-12}$ F/m), A is the overlapping electrode area, and d is the electrode gap. Expression E.3 can be used to calculate either multi-plate capacitor's nominal capacitance, i.e., the value of $C_1$ or $C_2$ for the state in which $C_1=C_2$ which ideally corresponds to balanced electrode gaps. In one embodiment, the nominal capacitance of electrostatic actuator 34 is calculated to be 0.80 pF, assuming $d'_1=d'_2=100$ μm and A=9.03 mm², where $d'_1$ and $d'_2$ are electrode gaps 162 and 164 of electrostatic actuator 34. In one embodiment, the nominal capacitance of capacitive displacement sensor 36 is calculated to be 1.1 pF, assuming $d_1=d_2=75$ μm and A=9.03 mm², where $d_1$ and $d_2$ are electrode gaps 166 and 168 of capacitive displacement sensor 36. In one embodiment, actuatable capacitive transducer 30 is designed such that A is single valued. A nominal capacitance of 1 pF is the rule-of-thumb cutoff for good design practice; therefore, actuatable capacitive transducer 30 is configured to be in the vicinity of the rule-of-thumb cutoff.

Replacing $C_1$ and $C_2$ in E.2 with $$\frac{\varepsilon_o A}{d_1} \text{ and } \frac{\varepsilon_o A}{d_2},$$

respectively, results in the following Expression E.4 for capacitive displacement sensor 36:

$$V_{out2} = \frac{d_2 - d_1}{d_2 + d_1}|V_m| = \frac{\Delta d}{\overline{d}}|V_m|; \quad \text{E.4}$$

where $\overline{d}$ is the constant mean of $d_1$ and $d_2$, and where $\Delta d$ (which can be of either sign) is the change in one electrode gap (e.g., the change in $d_2$) relative to the condition in which the electrode gaps are balanced ($d_1=d_2=\overline{d}$). The change in the other electrode gap (e.g., the change in $d_1$) relative to the balanced condition is identical in magnitude but opposite in sign. A small $\overline{d}$ is conducive to high displacement sensitivity, which is the reason, in one embodiment, for utilizing thinner dielectric spacers 74 and 76 for capacitive displacement sensor 36 relative to electrostatic actuator 34. Expression E.4 predicts $V_{out2}$ to be a perfectly linear function of $\Delta d$ over the entire range of displacement. But in practice, parasitic capacitance not dependent on $$\frac{\Delta d}{\overline{d}}$$

restricts satisfactory linearity to some range less than the full range about the balanced condition. In one embodiment, both first and second multi-plate capacitors 34 and 36 of actuatable capacitive transducer 30 (an equation analogous to E.4 is applicable to the displacement sensing function of electrostatic actuator 34) are satisfactorily linear over a displacement range of ±5 µm about the natural state of displaceable electrodes 42. Larger displacements have not been experimentally investigated as they are not necessary for quantitative in-situ TEM nanoindentation.

Focusing now on electrostatic actuation, the electrostatic force $F_e$ generated by a parallel-plate capacitor comprised of a displaceable electrode and a stationary electrode is given by the following Expression E.5:

$$F_e = \frac{\kappa_o}{(1-\delta/d_o)}V^2; \quad \text{E.5}$$

where V is the electrostatic actuation voltage across the two electrodes, $d_o$ is the electrode gap when V=0, $\delta$ is the displaceable electrode displacement from $d_o$, and where the electrostatic force constant $\kappa_o$ is given by Expression E.6 below:

$$\kappa_o = \frac{\varepsilon_o A}{2d_o^2}; \quad \text{E.6}$$

where $\varepsilon_o$ and A retain their previously expressed definitions. In general, $\delta$ can be of either sign depending on the nature of the force displacing the displaceable electrode; however, $F_e$ can only cause the displaceable electrode to be attracted to the stationary electrode on account of its $V^2$ dependence.

Assume V in E.5 corresponds to $V_1$ and that $V_2=0$. Also assume that conductive probe 60 is sufficiently blocked from moving so that $\delta=0$ always. Setting $d_o$ equal to a chosen 100 µm thickness of dielectric spacers 74 and 76 of electrostatic actuator 34 results in actuatable capacitive transducer 30 having an expected $\kappa_o$ of 4.0 nN/V$^2$ and an expected maximum blocked $F_e$ of 1.4 mN at $V_1$'s maximum of 600V. In one embodiment, the electrostatic force constant $\kappa_o$ and the maximum blocked $F_e$ of a built actuatable capacitive transducer 30 were determined to be 3.6 nN/V$^2$ and 1.3 mN, respectively, both reasonably close to expectation. The capacity to generate a maximum blocked $F_e$ in the vicinity of 1 mN is a good compromise between achieving high resolution in $F_e$ and generating enough $F_e$ to indent a wide variety of samples up to their maximum depth of electron transparency, which is the reason for utilizing thicker dielectric spacers 74 and 76 for electrostatic actuator 34 relative to capacitive displacement sensor 36 in one embodiment.

In reality, $\delta$ is permitted to change. Displacement of displaceable electrode 42 must be assumed to be increasingly positive when conductive probe 60 moves toward a sample in order to be compatible with expression E.5 above. A changing $\delta$ affects the scaling between $F_e$ and $V^2$ through the denominator of expression E.5, the scaling being increasingly enhanced when $\delta$ becomes increasingly positive and being increasingly diminished when $\delta$ becomes increasingly negative. In most instances, $V_2$ remains at zero while $V_1$ is being varied during the nanoindentation test, but $V_2$ being connected provides a benefit nonetheless. Often, the dominant contributor of noise to $V_1$ and $V_2$ is found to be in-phase AC line noise; therefore, the electrostatic force noise associated with AC line noise present on $V_2$ tends to cancel the electrostatic force noise associated with AC line noise of the same phase present on $V_1$.

Still assuming $V_2=0$, $F_e$ represents a total applied force (always positive if non-zero) equal to the contact force $F_c$ (positive if repulsive to adhere to convention) plus the spring force $F_s=k\delta$ (the customary minus sign is dropped for convenience), which is a consequence of the parallel loading configuration. Hence, the following Expression E.7 can be used to calculate the contact force:

$$F_c = F_e - k\delta \quad \text{E.7.}$$

Expression E.7 also applies to actuation with conductive indenter 62 far from a sample. In that case, $F_c=0$ and $F_e=k\delta$.

The snap-to-contact instability and the spark-gap instability must be kept in mind when actuating electrostatically. To simplify the following discussion, again assume $V_2=0$. The snap-to-contact instability refers to displaceable electrodes 42 suddenly snapping toward the electrostatic actuator's stationary electrode 80 with $V_1$ applied. The possibility of this happening can be deduced from electrostatic force gradient vs. spring constant considerations, and is predicted to occur when $d_1$ narrows to $\frac{2}{3}d_o$ (or equivalently when $\delta=\frac{1}{3}d_o$) if the resistance to motion obeys Hooke's law; a higher order resistance to motion retards this instability. The spark-gap instability refers to a spark crossing $d_1$ when the electric field strength given by the ratio of $V_1$ to $d_1$ exceeds a critical value, which has the highest likelihood when the snap-to-contact instability is reached, but which can happen even prior to reaching the snap-to-contact instability. The critical electric field strength depends on pressure and has the lowest value in the corona discharge region in the vicinity of $10^{-2}$-$10^{-3}$ torr; therefore, actuatable capacitive transducer 30 should not be actuated while pumping down to the ~$10^{-7}$ torr operating pressure of a TEM. Fortunately, the spark-gap instability is of much reduced concern at ~$10^{-7}$ torr. The instrument's software limits δ to 5 μm to ensure the snap-to-contact instability and the spark-gap instability never occurring.

Drive cards ordinarily used for Hysitron's three-plate capacitive transducers facilitate the electrical configurations of the first and second multi-plate capacitors 34 and 36 of actuatable capacitive transducer 30 and the following describes their employment in one embodiment. Electrostatic actuator 34 is electrically connected to a first drive card and capacitive displacement sensor 36 is electrically connected to a second drive card, the first and second drive cards being identical in design but different in implementation. Each of the first and second drive cards (one can be seen in the photograph of FIG. 4B) generates $+V_m$ and $-V_m$ and has the capacity for coupling electrostatic actuation voltages to these high-frequency modulation signals. The first drive card for electrostatic actuator 34 couples $V_1$ and $V_2$ supplied by a transducer controller to $+V_m$ and $-V_m$ generated by this drive card in the manner described above. The second drive card for capacitive displacement sensor 36 simply couples a ground signal supplied by the transducer controller to $+V_m$ and $-V_m$ generated by this drive card to disable electrostatic actuation.

Each of the first and second drive cards has a preamplifier having high input impedance and low output impedance. Each of the first and second drive cards also has circuitry for synchronous demodulation of the preamplifier's output as well as circuitry for subsequent low-pass filtering of the synchronous demodulator's output to generate a useful displacement signal. The first drive card's preamplifier receives $V_{out1}$ from electrostatic actuator 34. The second drive card's preamplifier receives $V_{out2}$ from capacitive displacement sensor 36. The first drive card ultimately outputs $V_{disp1}$ to the transducer controller for amplification and filtering beyond what is provided by this drive card, $V_{disp1}$ being its useful displacement signal. The second drive card ultimately outputs $V_{disp2}$ to the transducer controller for amplification and filtering beyond what is provided by this drive card, $V_{disp2}$ being its useful displacement signal. In general, $V_{disp1} \neq V_{disp2}$ but both represent δ if properly calibrated, e.g., via measurement of $V_{disp1}$ and $V_{disp2}$ vs. the displacement readout of an interferometer. In one embodiment, invoking a single modulation frequency of 130 kHz did not cause detectable coupling between $V_{disp1}$ and $V_{disp2}$. Separating the modulation frequency of the first drive card from that of the second drive card by several times the roll-off frequency of the post-demodulation low-pass filters can be employed to suppress coupling between $V_{disp1}$ and $V_{disp2}$ if problematic.

Points available on first and second multi-plate capacitors 34 and 36 for wire soldering are illustrated in FIG. 4A. Wires from the drive cards that carry the signals to be inputted to stationary electrodes 80 are soldered to stationary-electrode wire pads 170. Wires to the drive cards that carry the signals being outputted by displaceable electrodes 42 are soldered to displaceable-electrode wire tabs 108. Wires from the drive cards that carry the ground signal are soldered to the ground planes 84 of first and second multi-plate capacitors 34 and 36 and also to the conductive transducer body 32; these grounded elements serve as electrical shields. Wires from the drive cards that carry guard signals are soldered to guard-ring wire pads 172 (see FIG. 4A). The guard signal of electrostatic actuator 34 corresponds to the output of the first drive card's preamplifier, with both guard rings 82 of electrostatic actuator 34 receiving this guard signal. The guard signal of capacitive displacement sensor 36 corresponds to the output of the second drive card's preamplifier, with both guard rings 82 of capacitive displacement sensor 36 receiving this guard signal. The purpose is to guard the easily loaded signals present on displaceable electrodes 42. Perimeter holes 174, as shown in FIG. 4A facilitate wire routing. Cutouts 144 in conductive transducer body 32, as illustrated in FIG. 5B provide access to the soldering points after assembly of actuatable capacitive transducer 30, and also serve as venting for the purpose of evacuating air in a TEM.

Ordinarily, it is desirable to position the drive cards in very close proximity to the corresponding one of the first and second multi-plate capacitors 34 and 36 to minimize the length of wiring carrying the easily loaded signals being outputted by displaceable electrodes 42. However, placing the drive cards in high vacuum raises considerable thermal management and outgassing load issues. Consequently, the drive cards reside in the posterior of the TEM holder that remains at atmospheric pressure and results in a distance of approximately 1 ft between the drive cards and actuatable capacitive transducer 30 located at the anterior of the TEM holder Vacuum-compatible electrical feedthroughs facilitate the passage of wiring from atmospheric pressure into high vacuum. In spite of long wiring runs, actuatable capacitive transducer 30 performs well in a TEM through use of cabling having minimal capacitance between its conductors and its grounded shield. Moreover, the drive cards and the cabling are held such that they move with actuatable capacitive transducer 30 whenever actuatable capacitive transducer 30 is translated relative to the TEM holder. This avoids a change in electrical layout that might change the amount of capacitance between the conductors and the grounded shield of the cabling. Guarding rather than shielding the conductors carrying the signals being outputted by displaceable electrodes 42 has not been examined since guarding complicates the design of the cabling.

All materials associated with the actuatable capacitive transducer 30, including the adhesives (specialty epoxies), the materials of the cabling (copper, Teflon®, and brass), and the solder (silver), are sufficiently low in outgassing rate to be compatible with high vacuum. Furthermore, these materials are sufficiently low in ferromagnetic content to not cause undue difficulty when subjected to a strong magnetic field. Compatibility with these aspects of a TEM also means materials compatibility with a scanning electron microscope (SEM) for quantitative in-situ SEM nanoindentation. Although not yet verified, the built actuatable capacitive transducer is potentially compatible with use in ultra-high vacuum. Obviously, the materials of the built actuatable capacitive transducer are compatible with use in air or inert gas environments as well.

Figure 7:
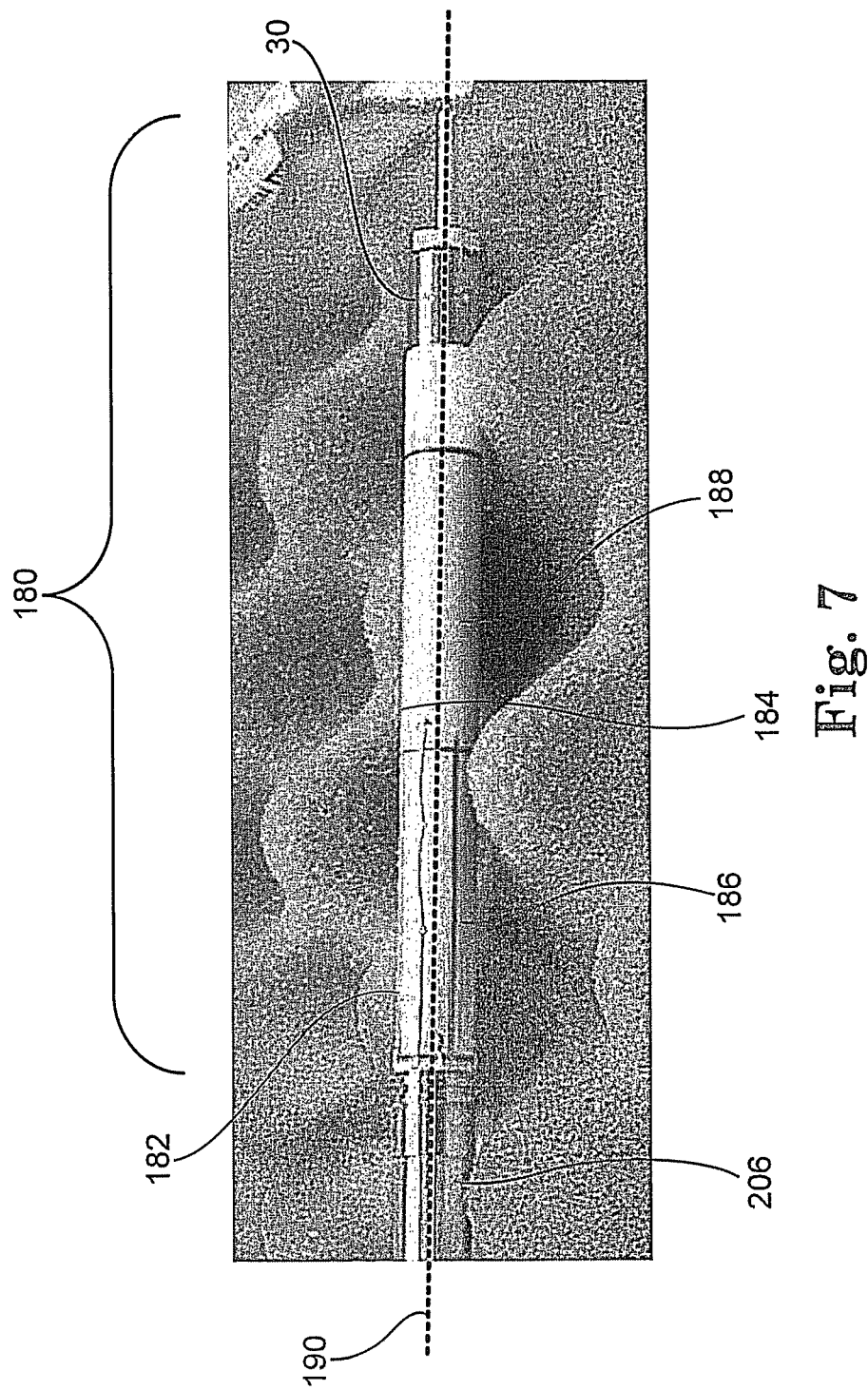
FIG. 7 is a photograph of a built nanoindentation head.

FIG. 7 is a photograph illustrating one embodiment of a nanoindentation head 180 according to the invention. As illustrated in FIG. 7, a nanoindentation head 180 comprises actuatable capacitive transducer 30 mechanically coupled to a 3D piezoelectric actuator 182. The 3D piezoelectric actuator 182 includes a one-piece piezoelectric (piezo) tube 184 comprised of an x-y segment 186 and a z segment 188; and has a hollow interior that serves as a conduit for the wiring to actuatable capacitive transducer 30. The z segment 188 is defined by an outer electrode (denoted $z_{outer}$) and an inner electrode (denoted $z_{inner}$) sandwiching the piezoelectric material. The x-y segment 186 is defined by four outer electrodes (denoted $+x_{outer}$, $-x_{outer}$, $+y_{outer}$, and $-y_{outer}$) and four inner electrodes (denoted $+x_{inner}$, $-x_{inner}$, $+y_{inner}$, and $-y_{inner}$) sandwiching the piezoelectric material. Voltages applied differentially to $z_{outer}$ and $z_{inner}$ will induce z segment 188 to extend or contract, thereby displacing actuatable capacitive transducer 30 along z axis 190 depicted in FIG. 7. A voltage applied to $+x_{outer}$ and $-x_{inner}$ and a voltage of the same magnitude but of opposite polarity applied to $-x_{outer}$ and $+x_{inner}$ will induce x-y segment 186 to bend, thereby displacing actuatable capacitive transducer 30 principally along the x axis, which is orthogonal to the z axis 190. Displacing actuatable capacitive transducer 30 principally along the y axis, which is orthogonal to the x and z axes involves an analogous application of voltages to the y electrodes.

In one embodiment, 3D piezoelectric actuator 182 of nanoindentation head 180 is made of a hard lead zirconate titanate (PZT) ceramic, where "hard" refers to a small $d_{31}$ piezoelectric constant, and its electrodes are of silver rather than of customary nickel to avoid nickel's ferromagnetism. Driven by a piezo controller capable of outputting differential voltages ranging from +370V to −370V, 3D piezoelectric actuator 182 of nanoindentation head 180 is capable of displacing actuatable capacitive transducer 30 ±55 μm along the x and y axes and ±4.7 μm along the z axis 190. The 3D piezoelectric actuator 182 is employed primarily as a sub-nm-resolution positioner, but it also participates in certain nanoindentation operating modes, and it can be used to raster scan the conductive indenter 62 to image a sample's surface in the manner of an AFM if desired. Although 3D piezoelectric actuator 182 currently does not employ a displacement sensor dedicated to measuring the extension or the contraction of z segment 188, the choice of a hard PZT ceramic helps to improve the reliability of correlating the motion provided to the differential voltage applied.

Nanoindentation head 180 is designed to be housed in a newly-developed TEM holder based largely on earlier TEM holders developed at National Center for Electron Microscopy/Lawrence Berkeley National Laboratory (NCEM/LBNL) for qualitative and semi-quantitative in-situ TEM nanoindentation (see References 6-11 and 13-17). Nevertheless, a TEM holder according to the present invention, as will be described in greater detail below, substantially outperforms these prior-art in-situ TEM nanoindentation holders, particularly with respect to load frame stiffness and coarse positioning stability, the latter aspect being related to the former aspect. In fact, Reference 10 and the erroneously titled Reference 9 pertain to taking advantage of poor load frame stiffness to deduce the contact force.

Figure 8A:
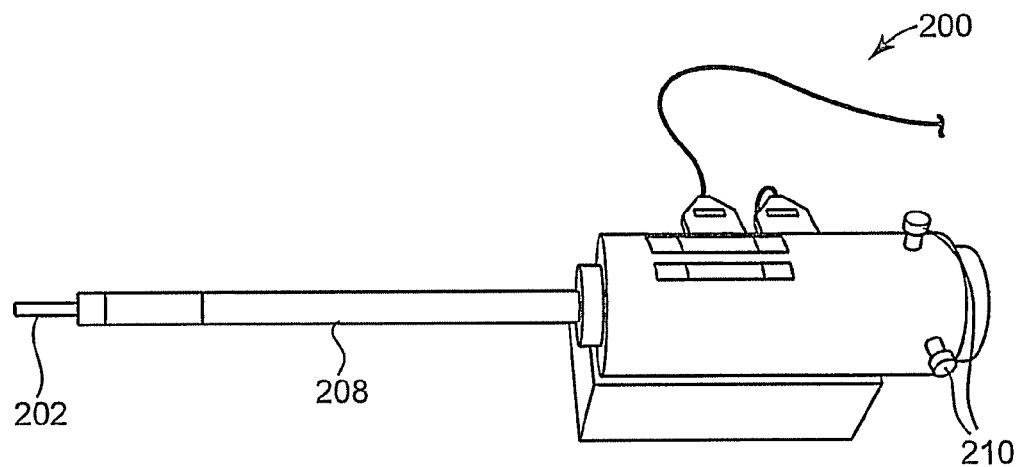
FIG. 8 is a built TEM holder: a) photograph of the holder shown in entirety; b) photograph showing the tongue portion of the holder in detail; and c) photograph showing the holder inserted into a JEOL JEM 3010 TEM.
Figure 8B:
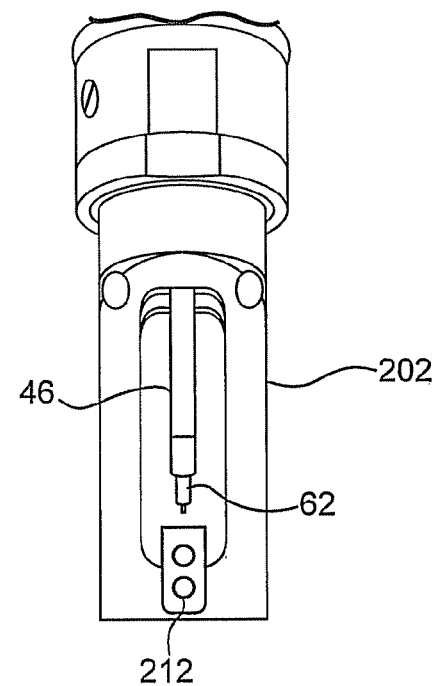
Figure 8C:
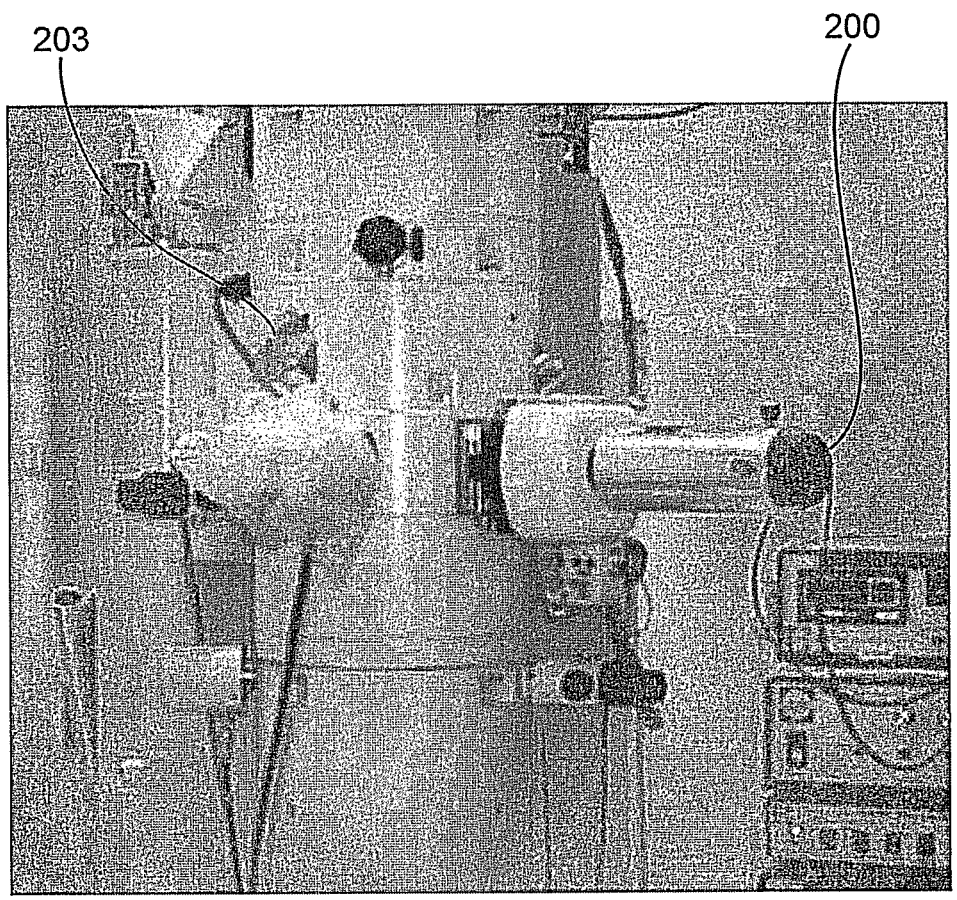

FIG. 8A is a photograph illustrating one embodiment of a TEM holder 200 according to the present invention. FIG. 8B is a photograph illustrating a tongue portion 202 of TEM holder 200. FIG. 8C is a photograph illustrating TEM holder 200 inserted into a TEM 203 with its posterior 204 visible. It is noted that TEM 203 illustrated in FIG. 8C comprises a JEOL JEM 3010 TEM. With reference to FIG. 7, nanoindentation head 180 includes an internal tube 206 which mechanically supports nanoindentation head 180. Internal tube 206 is internal to an external tube 208, which is illustrated in FIG. 8A. Also illustrated in FIG. 8A are three coarse positioning screws 210. Manually turning the three coarse positioning screws 210 causes the internal tube 206 to be positioned three dimensionally with respect to external tube 208, thereby causing the nanoindentation head 180 to be positioned three dimensionally with respect to tongue 202, which is most easily seen in FIG. 8B. In one embodiment, the resolution of coarse positioning is 200 μm/rev. In one embodiment, as illustrated by FIG. 8B, tongue 202 includes a sample clamp 212 to tightly hold a wedge-shaped sample, such as the one depicted in FIG. 11A below and illustrated as being indented by conductive indenter 62. Sample clamp 212 is easily detached from TEM holder 200 to facilitate screwing of conductive probe 60 on or off the portion of conductive threaded rod 48 protruding from coupling shaft 46 of actuatable capacitive transducer 30. Tongue 202 is the portion of TEM holder 200 that inserts into the narrow pole piece gap of a TEM. All objects penetrating tongue 202 must be confined to the dimensions of the tongue.

It is desirable to keep the sample stationary, especially when invoking nanoindentation operating modes involving 3D piezoelectric actuator 182 to affect the indenter-sample separation. Keeping the sample stationary enables the sample's region of interest to fully fill the TEM's field of view and eliminates the possibility of a portion of the sample's region of interest shifting out of the TEM's field of view during nanoindentation tests involving 3D piezoelectric actuator 182. In contrast, Nanofactory's instrument keeps its miniature two-plate capacitive transducer stationary while actuating its piezoelectric actuator carrying the sample to affect the indenter-sample separation (see Reference 20).

Figure 9:
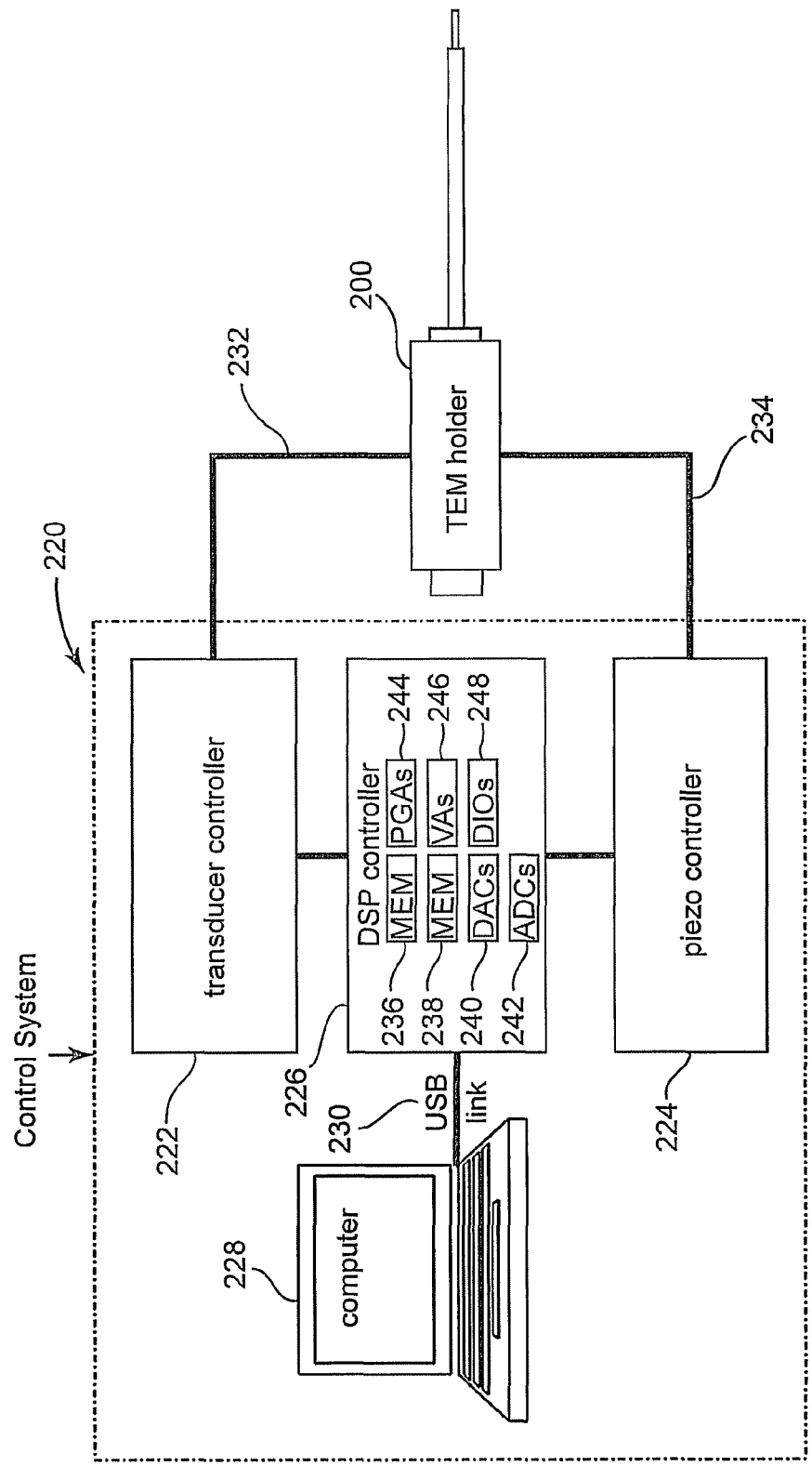
FIG. 9 is a block diagram for a nanoindentation head's control system.

FIG. 9 is a block diagram illustrating generally one embodiment of a control system 220 for nanoindentation head 180 according to the present invention. Control system 220 is comprised of a transducer controller 222 (as mentioned above), a piezo controller 224 (as mentioned above), a digital signal processor (DSP) based controller 226 capable of 100 million instructions per second, and a computer 228 running the instrument's software. Computer 228 is in communication with DSP controller 226 via a universal serial bus (USB) link 230. In one embodiment, computer 228 comprises a laptop computer. DSP controller 226 is in communication with transducer controller 222, which is cabled, as indicated at 232, to the drive cards of actuatable capacitive transducer 30 housed within the TEM holder 200, and with piezo controller 224, which is cabled, as indicated at 234, to 3D piezoelectric actuator 182 also housed within TEM holder 200. In one embodiment, transducer controller 222 and piezo controller 224 are based, in part, on units currently supplied with Hysitron's suite of nanoindenters. As a result, control system 220 is an enabler of imaging in the manner of an AFM in addition to being an enabler of nanoindentation tests. DSP controller 226, on the other hand, is an entirely new development.

DSP controller 226 is programmable and has a memory space 236 for storing instructions received from computer 228, and a memory space 238 for storing digitized data to be received by computer 228. DSP controller 226 also includes a plurality of 16-bit digital-to-analog converters (DACs) 240, a plurality of 16-bit analog-to-digital converters (ADCs) 242, a plurality of programmable gain amplifiers (PGAs) 244, a plurality of voltage attenuators (VAs) 246, and a plurality of digital input-output channels (DIOs) 248 to carry out its various programmed tasks. DACs 240 generate analog voltages which are amplified by PGAs 244. The outputs of the PGAs are further amplified either by transducer controller 222 to generate $V_1$ and $V_2$ to actuatable capacitive transducer 30 via the first drive card or by piezo controller 224 to generate the voltages to 3D piezoelectric actuator 182. ADCs 242 digitize analog voltages outputted by VAs 246, which receive certain analog signals to attenuate before digitization, including $V_{disp1}$ and $V_{disp2}$ as provided by transducer controller 222. The necessity of PGAs 244 and VAs 246 is linked to a mismatch in DAC 240 and ADC 242 saturation levels in comparison to transducer controller 222 and piezo controller 224 saturation levels. DIOs 248 are used to control chip states of various chips included in transducer controller 222, piezo controller 224, and DSP controller 226. DSP controller 226 generally executes control loops at a 22 kHz loop rate but can execute control loops at loop rates as high as 80 kHz. Several control loops provide the characteristic of active damping, a particularly important characteristic to provide when actuatable capacitive transducer 30 is operating in the extremely low damping environment of a TEM.

DSP controller 226 enables a variety of nanoindentation operating modes which represent methods of conducting quantitative in-situ TEM nanoindentation providing that a stream of TEM images that show how the sample deforms while being indented is viewed/recorded. The following is a list of at least six nanoindentation operating modes capable of being performed by control system 220:

1. Load control mode—utilize either a feedback control algorithm (e.g., proportional-integral-derivative or PID) or a feedforward augmented feedback control algorithm with optionally adaptive characteristics to adjust $V_1$ ($V_2$=0) in a manner that causes the contact force to meet a predetermined contact force vs. time function while keeping 3D piezoelectric actuator 182 static. The development of this mode for Hysitron's three-plate capacitive transducer has been described in Reference 4.
2. Displacement control mode—utilize either a feedback control algorithm or a feedforward augmented feedback control algorithm with optionally adaptive characteristics to adjust $V_1$ ($V_2$=0) in a manner that causes the indenter displacement to meet a predetermined indenter displacement vs. time function while keeping 3D piezoelectric actuator 182 static. The development of this mode for Hysitron's three-plate capacitive transducer also has been described in Reference 4.
3. Single-sided force-feedback control mode (another form of displacement control)—conduct single-sided force-feedback control involving fed-back adjustments to $V_1$ ($V_2$=0) while varying the differential voltage to the z segment 188 of 3D piezoelectric actuator 182 to affect the indenter-sample separation. This mode is analogous to the torque balance operation of the IFM in the sense that displaceable electrodes 42 are suppressed from deflecting.
4. Double-sided force-feedback control mode (yet another form of displacement control)—conduct double-sided force-feedback control involving coordinated fed-back adjustments to $V_1$ and $V_2$ while varying the differential voltage to the z segment 188 of 3D piezoelectric actuator 182 to affect the indenter-sample separation. This mode also is analogous to the torque balance operation of the IFM in the sense just mentioned. However, this mode in conjunction with actuatable capacitive transducer 30 has a certain novel advantage over the torque balance operation of the IFM, which will be explained in greater detail below.
5. Open-loop mode (an open-loop approximation of load control)—vary $V_1$ ($V_2$=0) in an open-loop manner in accordance with a predetermined blocked electrostatic force vs. time function while keeping 3D piezoelectric actuator 182 static. This is the traditional nanoindentation operating mode of Hysitron's three-plate capacitive transducer.
6. Spring-force mode—do not actuate the electrostatic actuator 34 ($V_1$=$V_2$=0) and measure the spring force that relates to the contact force while varying the differential voltage to the z segment 188 of 3D piezoelectric actuator 182 to affect the indenter-sample separation. Disconnecting the electrostatic actuation circuitry from electrostatic actuator 34 before executing this mode will eliminate spring force noise derived from electrostatic force noise. This mode is reminiscent of an AFM or Nanofactory's instrument attempting to conduct nanoindentation.

The following assumes that the relevant electrostatic force constant is calibrated rather than calculated from geometric parameters. Nanoindentation operating modes numbered 1, 2, and 5 in the above list require knowledge of $\kappa_o$, $d_o$, and $k$ to calculate $F_c$ because displaceable electrodes 42 are displaced during the nanoindentation test (see Expression E.7 in conjunction with Expression E.5). Mode number 3 from the above list requires knowledge of $\kappa_o$ and $d_o$ to calculate $F_c$, but not k because displaceable electrodes 42 are suppressed from displacing during the nanoindentation test. The not obvious necessity of knowing both $\kappa_o$ and $d_o$ in the case of mode numbered 3 will be explained in greater detail below. Mode number 4 from the above list requires knowledge of a $K_b$ corresponding to the electrostatic force constant for the balanced condition to calculate $F_c$, but not k or $\bar{d}$ (the balanced condition's analog to $d_o$) because displaceable electrodes 42 are suppressed from displacing during the nanoindentation test; a contact force equation utilizing $\kappa_b$ will be provided in the next paragraph. Mode number 6 from the above list does not require knowledge of $\kappa_o$ or $d_o$ because this mode does not involve generation of electrostatic force, but obviously requires the knowledge of k to calculate $F_c$. Of course, the above list is not exhaustive. For example, it is also possible to invoke modes involving variations in $V_1$ and $V_2$ that cause $\delta$ to change while keeping 3D piezoelectric actuator 182 static, but such modes are more complicated to calibrate than the others.

The following begins a detailed explanation of the novel advantages of the double-sided force-feedback control mode over the torque balance operation of the IFM. First, assume electrostatic actuator 34 is endowed with perfectly balanced electrode gaps at $V_1$=$V_2$=0 when conductive indenter 62 is far removed from the sample. Next, assume the electrode gaps of electrostatic actuator 34 remain balanced after equating both $V_1$ and $V_2$ to a bias voltage $V_o$ (preferably 300V), conductive indenter 62 still being far removed from the sample. Additionally, assume $V_1$=$V_o$+$V_{fb}$ and $V_2$=$V_o$−$V_{fb}$ when using this nanoindentation operating mode, where $V_{fb}$ is a fed-back adjustment to $V_1$ and $V_2$, which is restricted to the range of ±$V_o$, and which keeps the electrode gaps of electrostatic actuator 34 balanced in the presence of $F_c$. With this scenario, $V_{fb}$ is zero when conductive indenter 62 is far removed from the sample, and is negative or positive when $F_c$ is attractive or repulsive, respectively. Setting the sum of the electrostatic force owing to $V_1$, the electrostatic force owing to $V_2$, and $F_c$ to zero yields the following Expression E.8 for the contact force:

$$F_c = 4\kappa_b V_o V_{fb} \quad \quad \text{E.8;}$$

which means $F_c$ is a linear function of $V_{fb}$. In practice, achieving a high degree of linearity requires maintaining the electrode gaps of electrostatic actuator 34 (rather than the electrode gaps of capacitive displacement sensor 36) at the balanced condition, which is the motivation for utilizing electrostatic actuator 34 as an additional capacitive displacement sensor.

The following continues the detailed explanation of the novel advantages of the double-sided force-feedback control mode over the torque balance operation of the IFM. In the case of the IFM, it is the sum of the torques rather than of the forces that is directly pinned to zero by the action of the electrostatic-force-feedback controller. Keeping this in mind, let's examine the IFM sensor being controlled in a manner analogous to the double-sided force-feedback control mode of the present invention. With this assumption, setting the sum of the torques to zero (again assuming inherently balanced electrode gaps) yields Expression E.9 below:

$$F_c = 4\kappa_b V_o V_{fb} L/L' \qquad \text{E.9};$$

where L is the moment arm from either electrostatic force to the torsion bar axis and L' is the moment arm from the indenter to the torsion bar axis. Hence, the IFM also is capable of operating in a manner in which $F_c$ is a linear function of $V_{fb}$. However, achieving linearity comes with a difficulty: the sum of the indenter-side electrostatic force $\kappa_b(V_o-V_{fb})^2$, the non-indenter-side electrostatic force $\kappa_b(V_o+V_{fb})^2$, and $F_c$ is not kept at the initial sum of these forces equaling $2\kappa_b V_o^2$. In fact, the change in the sum of these forces relative to $2\kappa_b V_o^2$ is given by $F_c+2\kappa_b V_{fb}^2$ which clearly is nonzero in general. As a consequence, the torsion bars will deflect in a manner resulting in the electrode gaps uniformly expanding or collapsing, with the amount of this unintended deflection being dictated by the associated restoring force of the torsion bars equilibrating with the change in the sum of the electrostatic forces and $F_c$. The electrode gaps expanding or collapsing uniformly results in an atypical mechanical compliance not directly detectable by the IFM, and introduces error in the calculation of $F_c$ because Expression E.9 assumes the electrode gaps to be invariant.

The following concludes the detailed explanation of the novel advantages of the double-sided force-feedback control mode over the torque balance operation of the IFM. As it turns out, the only way of eliminating the atypical source of mechanical compliance is to fix the non-indenter-side electrostatic force to $\kappa_b V_o^2$ and set L and L' to be equal. With this configuration, Expression E.10 yields:

$$F_c = 2\kappa_b V_o V_{fb} - \kappa_b V_{fb}^2 \qquad \text{E.10};$$

which means $F_c$ is no longer a linear function of $V_{fb}$. Obviously, the double-side force-feedback control mode in combination with actuatable capacitive transducer 30 (or in combination with any other nanoindentation transducer comprising a stacked three-plate electrostatic actuator, such as Hysitron's three-plate capacitive transducer, for example) is an improvement over any form of torque balance operation of the IFM.

The wide variety of nanoindentation operating modes feasible for use with control system 220 of nanoindentation head 180 are not equally worthy when conducting nanoindentation tests in a TEM. Reference 4 describes the overwhelming superiority of displacement control over load control if the goal is to investigate discrete deformation phenomena such as the onset of plasticity, likely an impetus for quantitative in-situ TEM nanoindentation experimentation. Furthermore, displacement control rather than load control provides nanoindentation data that can be directly compared to molecular dynamics simulations and finite element modeling of nanoindentation-induced deformation, also likely an impetus for quantitative in-situ TEM nanoindentation experimentation. Modes numbered 2-4 in the above list are variations of displacement control, but those numbered 3 and 4 require an additional displacement sensor dedicated to measuring the extension or contraction of 3D piezoelectric actuator 182 to achieve high penetration depth accuracy. Consequently, mode numbered 2 represents the simplest path to quantitative displacement-controlled force-displacement curves. However, modes numbered 3 and 4 are superior from the viewpoint of transducer control performance because it is easier to simply fend off forces attempting to deflect displaceable electrodes 42 in comparison to meeting an indenter displacement demand ramp, as is the case with mode number 2. Mode number 3 does require $V_1 > 0$ before engaging a sample in order to have a range of $V_1$ in reserve for fending off attractive forces acting on conductive indenter 62.

Mode numbered 4 (the other force-feedback control mode) does not require a similar consideration on account of it being inherently bidirectional in terms of net electrostatic force, although this mode will involve a background $V_{fb}$ to balance the electrode gaps of electrostatic actuator 34 if these electrode gaps are not inherently balanced. The presence of a large background $V_{fb}$ will significantly alter the range of $V_{fb}$ remaining to counter forces acting on conductive indenter 62. A negative background $V_{fb}$ is preferable over a positive one because a typical nanoindentation test involves attractive forces that pale in comparison to the maximum in repulsive force. This aspect should be considered when constructing actuatable capacitive transducer 30.

As for load control, mode number 5 from the above list (an open-loop approximation of load control) provides an advantage over mode number 1 (true load control) in the sense that the former can be initiated from the out-of-contact condition, whereas the latter requires being in contact to achieve feedback loop closure. It is desirable to have the option of initiating nanoindentation tests from the out of condition (also a characteristic of modes numbered 2-4 and 6) in light of our quantitative in-situ TEM nanoindentation results revealing a single nanograin of aluminum plastically deforming upon first contact. Mode number 5, however, does have two distinct disadvantages in comparison to mode number 1. Firstly, in the case of mode number 5, the achieved $F_c$ will not exactly match the desired $F_c$, the usually small difference being related to $F_s$ and the dependence of $F_e$ on δ. Secondly, open-loop modes of operation (mode number 6 included) do not provide an opportunity to tune a feedback loop to damp actuatable capacitive transducer 30 in the high-vacuum environment of a TEM. As will be demonstrated, an optimally tuned feedback loop dramatically decreases the settling time of actuatable capacitive transducer 30 in this very low damping medium.

As for mode number 6, it falls outside the domain of quantitative nanoindentation on account of the series loading configuration it adopts. Furthermore, this mode does not enable dictating either a well-defined penetration depth rate or a well-defined contact force rate, a significant drawback if testing rate sensitive materials. Further, this mode is subject to the well-known jump-to-contact phenomenon that can happen during initial sample approach. Further still, this mode necessitates an additional displacement sensor dedicated to measuring the extension or contraction of 3D piezoelectric actuator 182 to achieve the best possible performance. But in spite of these numerous difficulties, mode number 6 still is useful because it is the mode most capable of detecting extremely small forces, providing the electrostatic actuation circuitry is disconnected from electrostatic actuator 34.

Switching between various nanoindentation operating modes during a nanoindentation test is a possibility. For example, it is feasible to start the nanoindentation test in the load control mode (mode number 1) to maintain $F_c$ at a specific small repulsive value for the purpose of measuring the rate of positional drift, then switch to the displacement control mode (mode number 2) to detach conductive indenter 62 from the sample by a specified distance, then reengage the sample in the displacement control mode (mode number 2) to the specific small repulsive value or to some other repulsive value, then switch to the load control mode (mode number 1) to increase $F_c$ to the desired maximum load and to subsequently decrease $F_c$ to the specific small repulsive value or to some other repulsive value, then switch to the displacement control mode (mode number 2) to detach conductive indenter 62 from the sample by a specified distance. This scenario allows for data correction with regard to positional drift (see Reference 21), and provides data possibly showing attractive interaction forces during the reengagement step, and provides data for better establishing the position of the sample's surface which defines the zero point of the nanoindentation test (see Reference 21), and provides data possibly showing adhesive forces (also attractive) as conductive indenter 62 detaches from the sample for the final time, while conducting the bulk of the nanoindentation test in the load control mode (mode number 1). Of course, $V_1$ must be greater than zero before engaging the sample prior to the nanoindentation test in order to have enough $V_1$ in reserve to be able to chase positional drift of either sign and to be able to guarantee the ability to detach conductive indenter 62 from the sample. Here, engaging the sample prior to the nanoindentation test involves the use of 3D piezoelectric actuator 182 to displace actuatable capacitive transducer 30 towards the sample until achieving the specific small repulsive value.

The following Expression E.11 can be used to calculate the contact force for the case of $V_1$ intentionally greater than zero before engaging the sample in conjunction with $V_2=0$ throughout the nanoindentation test:

$$F_c = \frac{\kappa_o}{[1-(\delta'+\delta_{offset})/d_o]^2}(V'+V_{offset})^2 - \frac{\kappa_o}{(1-\delta_{offset}/d_o)^2}V_{offset}^2 - k\delta'; \quad \text{E.11}$$

where $V_{offset}$ is the value of $V_1$ before engaging the sample, $V'$ is the change in $V_1$ from $V_{offset}$, $\delta_{offset}$ is the value of $\delta$ owing to $V_{offset}$, $\delta'$ is the change in $\delta$ from $\delta_{offset}$, and where the remaining parameters have been defined already. In the case of the single-sided force-feedback control mode (mode number 3), the value of $V'$ is whatever is necessary to maintain $\delta$ at zero. The necessity of knowing both $\kappa_o$ and $d_o$ in this case stems from the need to calculate the term $$\frac{\kappa_o}{(1-\delta_{offset}/d_o)^2}$$

for any chosen value of $V_{offset}$. The instrument's software treats $V_{offset}$ as an adjustable parameter to allow the user to balance having a sufficient reserve in $V_1$ against shrinking the range of $V'$.

Returning to the jump-to-contact phenomenon, conductive indenter 62 will jump into contact with the sample if the gradient of the attractive force acting on conductive indenter 62 exceeds the spring constant of actuatable capacitive transducer 30. The occurrence of jump-to-contact prevents force-displacement measurement over the entire range of indenter-sample separation. Mode number 5 also is subject to the jump-to-contact phenomenon, whereas mode numbers 2-4 are stable against jump-to-contact on account of the displacement control they provide. However, no mode can stop atoms of the sample's surface from jumping into contact with conductive indenter 62 if they desire to do so. As for mode number 1, the jump-to-contact phenomenon is irrelevant because mode number 1 requires being in repulsive contact before being initiated.

The combination of nanoindentation head 180, which comprises actuatable capacitive transducer 30 and 3D piezoelectric actuator 182, TEM holder 203, and nanoindentation head 180 control system 220 helps define a quantitative in-situ TEM nanoindenter. Numerous performance aspects of a built quantitative in-situ TEM nanoindenter were investigated in a JEOL JEM 3010 TEM located at NCEM/LBNL over the time period of Mar. 23-25, 2005. NCEM/LBNL is a facility of the Department of Energy and a confidentiality agreement is in place with this facility. Unless indicated otherwise, the performance results that follow were obtained in this particular TEM. Obviously, all components specified in the description of the performance results are built components.

To quantify baseline noise characteristics, out-of-contact force and displacement vs. time traces were acquired in a measurement bandwidth typical of nanoindentation tests. From these traces, the out-of-contact force noise floor was estimated to be 0.11 µN RMS while using the open-loop mode with $V_1=0$, and 0.16 µN RMS while using the displacement control mode with the demanded $\delta$ kept constant. From the same traces, the out-of-contact displacement noise floor was estimated to be 0.41 nm RMS while using the open-loop mode, and 0.48 nm RMS while using the displacement control mode. These values are considerably above the limits for thermally-driven mechanical noise in the same measurement bandwidth, yet are indicative of a high-performance nanoindenter. The out-of-contact noise floors were not affected by the status of the 300 kV electron beam (impinging the conductive indenter vs. turned off) or by the choice of magnification mode (low vs. high).

Use of the displacement control mode caused a moderate increase in the out-of-contact noise floors; however, this mode and the other modes invoking feedback were extremely beneficial in terms of improving the time to settle after encountering a transient disturbance. FIG. 10A illustrates an out-of-contact impulse-ring-down trace 250 for the open-loop mode ($V_1=0$) with the vacuum pressure in the range of $10^{-7}$ torr. Based on the exponential decay of the trace's envelope, the Q in high vacuum is 6000 in comparison to only 25 in an air environment. As a consequence, the elapsed time to a 99% settled displacement signal is an unacceptably long 66 s. FIG. 10B provides an out-of-contact step-response trace 252 while using the displacement control mode with the vacuum pressure in the range of $10^{-7}$ torr; a step change in the demanded $\delta$ initiated the step response. The benefit of closed-loop operation is clearly evident in that the elapsed time to a 99% settled displacement signal is reduced from an unacceptably long 66 s to a mere 13 ms.

A hand turning any of coarse positioning screws 210 of the TEM holder 200 was found to be a significant source of potentially damaging transients. On several occasions, conductive indenter 62 visibly damaged the sample while coarse positioning, the result of high-amplitude ringing in high vacuum set off by the action of the hand. Of note, all such occurrences corresponded to using the open-loop mode. Apparently, closed-loop control prevented large swings in indenter displacement even during the rough act of coarse positioning. Closed-loop control also suppressed ringing following a sudden change in how a sample responded to a nanoindentation test.

The stability of the natural state of displaceable electrodes 42 against rotation of TEM holder 200 about its central axis was tested over the physically possible range of 0-28°. The change in the displacement signals was only 46.8 nm over the full range of rotation, which indicated an extremely horizontal alignment with respect to gravity. The stability of the natural state also was tested against the status of the electron beam. The electron beam impinging conductive indenter 62 did not affect the displacement signals relative to their values with the electron beam turned off. However, the displacement signals were noticeably impacted by the choice of magnification mode. Switching from low to high magnification mode reproducibly caused the displacement signals to shift by an amount corresponding to 1.03 μm towards the electron beam. Fortunately, the shift was invariant as long as the magnification mode remained unchanged.

A shift by 1.03 μm is not unacceptable, but does require onsite re-determination of the electrostatic force calibration function for certain nanoindentation operating modes. The instrument's software possesses an algorithm designed to optimize the electrostatic force calibration function so that post-shift, out-of-contact force-displacement curves will yield the proper value for k. A shift significantly much greater than 1.03 μm would be intolerable, especially for the case of the double-sided force-feedback control mode.

The displacement signals in the low magnification mode were comparable to their values for horizontal alignment outside the TEM. This observation is consistent with a weak to nonexistent local magnetic field when in the low magnification mode, and a strong local magnetic field when in the high magnification mode. Trace levels of ferromagnetic impurities in components of actuatable capacitive transducer 30 likely participated in the coupling to the magnetic field. The titanium shaft of conductive probe 60 possesses by far the highest ferromagnetic content in terms of concentration, iron impurities at the level of 0.3 wt %, and in terms of total number of ferromagnetic atoms. Hence, an ultrapure titanium shaft might substantially reduce coupling to the magnetic field.

Figure 11A:
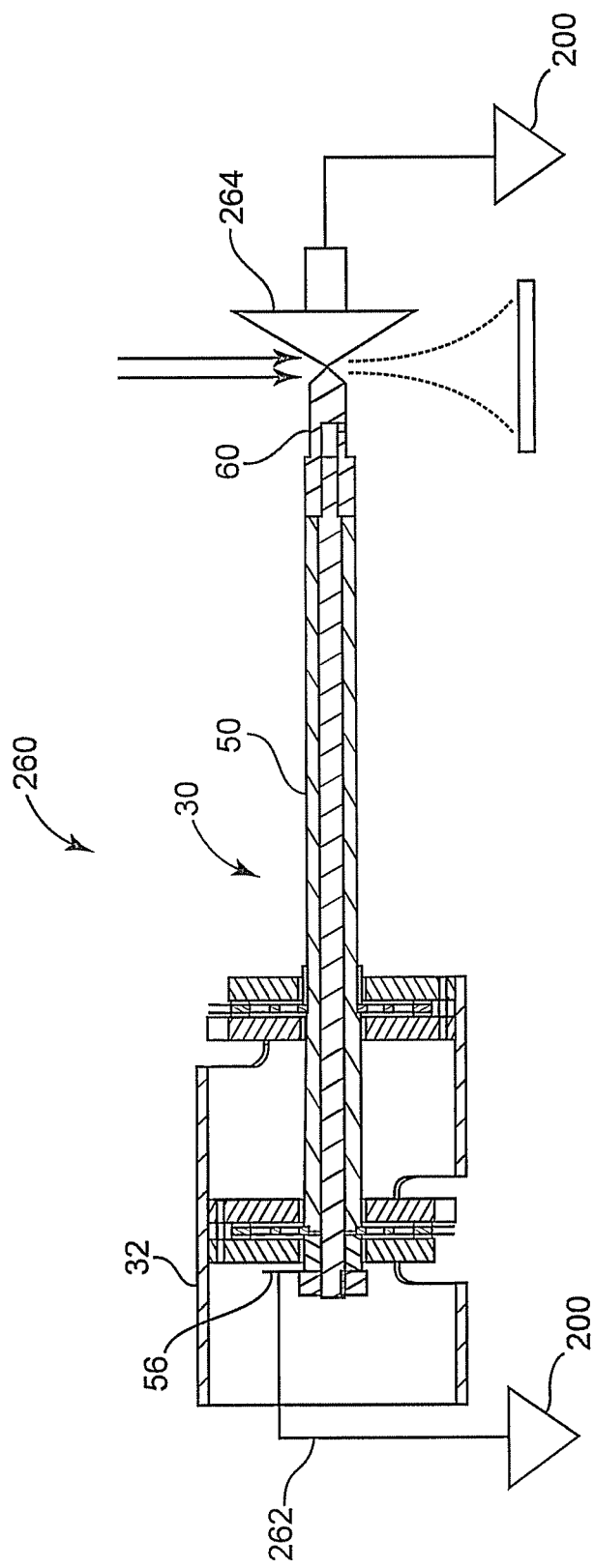
FIG. 11 illustrates means for bleeding charge from a conductive indenter when operating in a JEOL JEM 3010 TEM and compares quantitative in-situ TEM cantilever bending data for two electrical configurations: a) drawing of a proper electrical configuration; b) force-displacement curve while using the displacement control mode, for an improper electrical configuration; and c) force-displacement curve while using the displacement control mode, for the proper electrical configuration depicted in a).

FIG. 11A illustrates one embodiment of an electrical configuration 260 found to be compatible with the JEOL JEM 3010 TEM for bleeding charge from conductive indenter 62. As can be seen in FIG. 11A, conductive indenter 62, the remainder of conductive probe 60, conductive threaded rod 48, and a probe wire 262 soldered to the probe wire tab 56 in intimate electrical contact with conductive threaded rod 48 form an electrical path to TEM holder 200. FIG. 11A also shows a sample 264 electrically connected to TEM holder 200 to ensure that the sample and conductive indenter 62 are nominally at the same electrical potential, via good electrical continuity between sample clamp 212 and the point at which the probe wire attaches to TEM holder 200. Probe wire 262 must be highly flexible in order to not impede the motion of displaceable electrodes 42.

TEM holder 200 could not be grounded to control system 200 of nanoindentation head 180 as doing so sounded an alarm originating from the TEM. However, electrically connecting the conductive transducer body 32 of actuatable capacitive transducer 30 and ground planes 84 to the ground of control system 220 did not sound the alarm because these components were kept electrically isolated from TEM holder 200. Apparently, electrically connecting TEM holder 200 to the ground of control system 220 is interpreted by the TEM as a crash of TEM holder 200 into a pole piece.

Figure 11C:
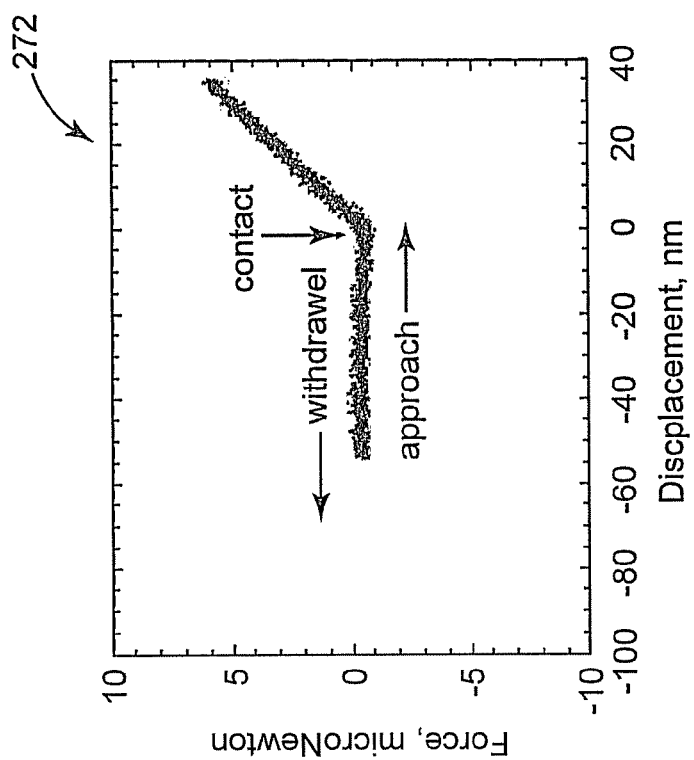
Figure 11B:
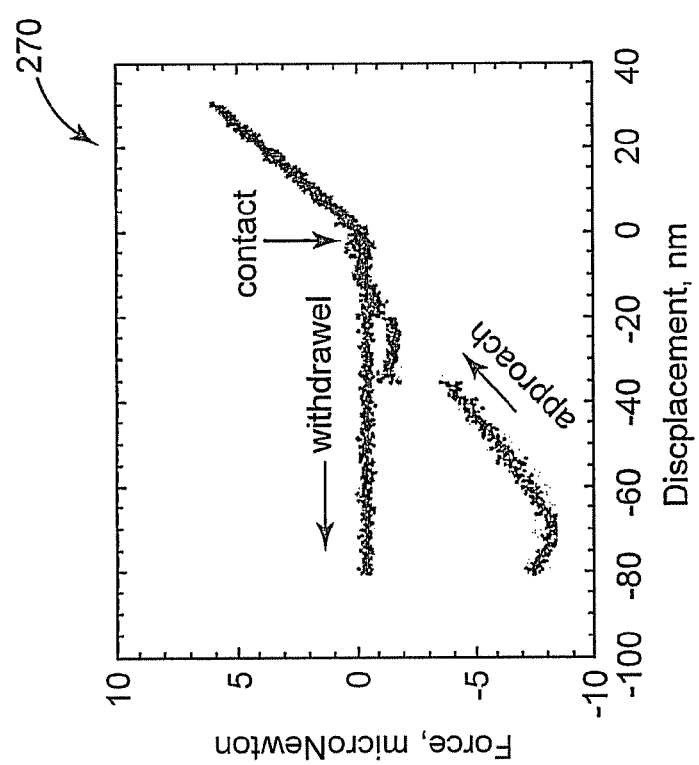

FIGS. 11B and 11C show force-displacement curves 270 and 272 while using the displacement control mode, which correspond to conductive indenter 62 first approaching then withdrawing from the tip of a plank-type silicon AFM cantilever while the TEM imaged both conductive indenter 62 and the tip of the cantilever. The curve in FIG. 11B illustrates the detrimental impact of not electrically connecting conductive indenter 62 to a charge sink of any type, whereas the curve in FIG. 11C is an example of a proper mechanical response. Measuring a proper mechanical response required both conductive indenter 62 and the AFM cantilever (product no. NSC15/No Al from μmasch) being nominally at the same electrical potential.

In FIG. 11B, the significant attractive (negative) forces seen in the initial portion of the approach segment likely are the consequence of conductive indenter 62 and the AFM cantilever absorbing different amounts of charge from the electron beam. The subsequent lack of attractive forces throughout the withdrawal segment likely is evidence for charge equilibration once repulsive contact (yielding positive forces) has been made. Interestingly, the observation of at least two discrete decreases in attractive force during the initial portion of the approach segment is suggestive of discrete charge transfer events occurring prior to making repulsive contact. FIG. 11C, in comparison, does not show significant attractive forces over any portion of the curve. Moreover, the approach segment data and the withdrawal segment data in FIG. 11C are virtually identical. Apparently, TEM holder 200 serves as a sufficient charge sink even when not electrically connected to the ground of control system 220 of nanoindentation head 180.

To ascertain the ability of actuatable capacitive transducer 30 to maintain its metrological accuracy in the TEM environment, a number of force-displacement curves while using the displacement control mode were acquired with conductive indenter 62 against the tip of the AFM cantilever while imaging with the TEM. The initial slope of these force-displacement curves was consistent with an AFM cantilever spring constant of 50.6±0.8N/m at the tip location. In comparison, a value of 50.9N/m at the tip location was obtained by inputting the AFM cantilever's dimensions (measured from SEM images) into the well-known cantilever bending equation. The high level of agreement between measured and calculated AFM cantilever spring constants indicated the TEM environment did not impact the metrological accuracy of actuatable capacitive transducer 30.

The following is an example of methodology preceding quantitative in-situ TEM nanoindentation tests on wedge-shaped samples, such as wedge-shaped sample 264 depicted in FIG. 11A, which have a plateau generally in the range of 100 nm in width and macroscopic dimension in length. First, TEM holder 200 is translated and rotated to achieve optimized TEM images of sample 264. Next, the TEM's magnification is adjusted to provide a large enough field of view such that both conductive indenter 62 and sample 264 can be seen at the same time. Next, coarse positioning screws 210 of TEM holder 200 are adjusted to bring conductive indenter 62 close enough to sample 264 to be well within the range of motion of 3D piezoelectric actuator 182, while adjusting the TEM's magnification as needed. Any of the variations of displacement control can be used during coarse positioning to prevent large swings of displaceable electrodes 42 in response to the action of the hand adjusting coarse positioning screws 210. Next, 3D piezoelectric actuator 182 is used to position conductive indenter 62 to within a nanoscale distance to a point on the plateau centered with respect to the plateau's width, again adjusting the TEM's magnification as needed, The desired nanoindentation operating mode, usually one of the variations of displacement control, can be selected during this process of fine positioning. Next, the nanoscale gap between conductive indenter 62 and the plateau is observed for a period of time to ensure that it is stable. Once found to be stable, the nanoindentation test is initiated to indent the selected point on the plateau centered with respect to the plateau's width. Conducting a nanoindentation test in the load control mode (mode number 1) requires using 3D piezoelectric actuator 182 to place conductive indenter 62 in minimal repulsive contact with the plateau before initiating the nanoindentation test.

Figure 12B:
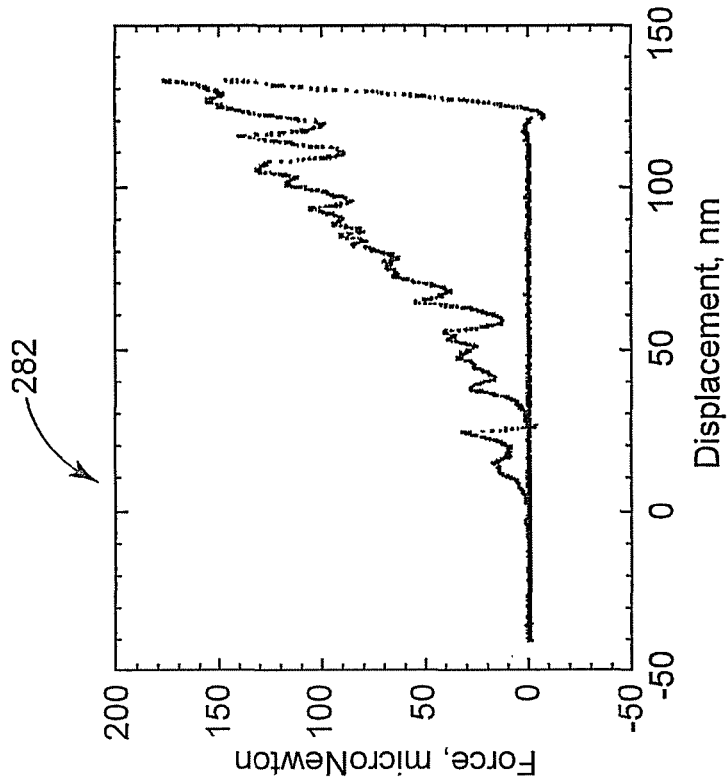
FIG. 12 is a set of quantitative in-situ TEM nanoindentation data for nanograin aluminum obtained with a built actuatable capacitive transducer operating in a JEOL JEM 3010 TEM: a) force-displacement curve while using the displacement control mode; b) force-displacement curve while using the single-sided force-feedback control mode; and c) two video frames extracted from a recorded stream of TEM images that correlates to the force-displacement curve in a).
Figure 12A:
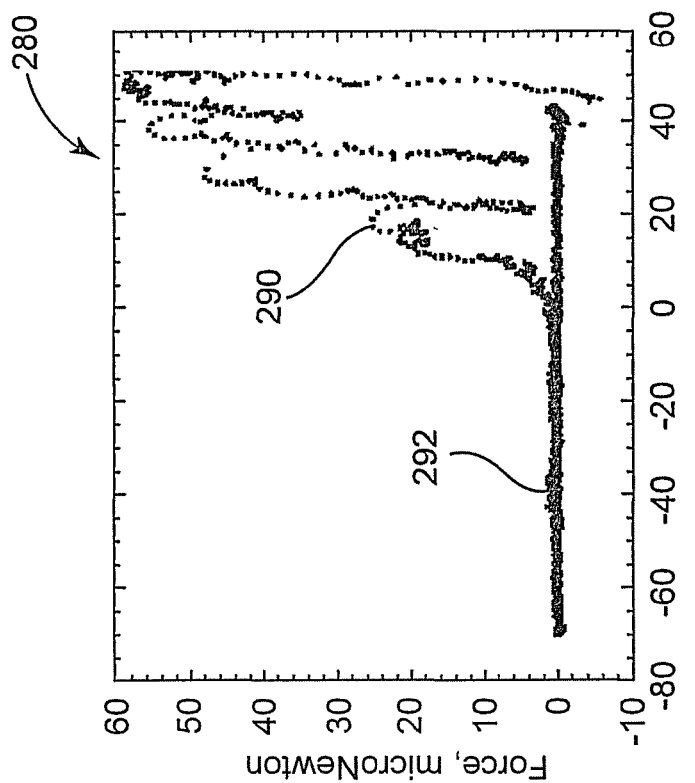

The following is a first example of quantitative in-situ TEM nanoindentation results that demonstrate the quantitative in-situ TEM nanoindenter's capability of investigating fundamental aspects of nanoscale material deformation. FIGS. 12A and 12B provide two examples of force-displacement curves 280 and 282 corresponding to a boron-doped diamond indenter of the Berkovich geometry indenting a nanograin of an aluminum film deposited on a wedge-shaped, single-crystal silicon substrate. Curve 280 in FIG. 12A was acquired while using the displacement control mode, whereas curve 282 in FIG. 12B was acquired while using the single-sided force-feedback control mode. Both curves 280 and 282 are dominated by repulsive forces, but both indicate relatively strong attractive adhesive forces during the final act of withdrawing conductive indenter 62 from the aluminum nanograin.

Signals digitized during a nanoindentation test can include signals indicative of electrostatic actuation voltage, signals indicative of displaceable electrode displacement, and a signal indicative of the extension or the contraction of z segment 188 of 3D piezoelectric actuator 182. Time also is recorded. The TEM images provided in FIG. 12C correspond to two video frames 284 and 286 extracted from a stream of TEM images recorded during the process of acquiring the force-displacement curve 280 in FIG. 12A. Left hand video frame 284 of FIG. 12C shows the aluminum nanograin about to be indented to be initially dislocation free, whereas right hand video frame 286 of FIG. 12C shows that dislocations confined to the aluminum nanograin on account of a difficulty in traversing the grain boundary have been nucleated and multiplied during the process of nanoindentation.

Focusing on force-displacement curve 280 of FIG. 12A, there are several discrete load drops that occur during the process of increasing the penetration depth, where each discrete load drop corresponds to sudden stress relaxation accompanying a sudden change in the aluminum nanograin's subsurface dislocation structure, as indicated by time correlation of the force-displacement curve to the recorded stream of TEM images. This particular experimental result is the first to conclusively link discrete load drops to discrete dislocation nucleation and multiplication events. However, surprisingly, the first large discrete load drop, indicated at 290, is not the one associated with the onset of plasticity, an observation at odds with the belief of many researchers. Instead, the onset of plasticity is coincident with the small force transient, indicated at 292. Video frames 284 and 286 provided in FIG. 12C are sequential video frames of this initial dislocation nucleation and multiplication event. The conclusion reached here would not have been possible without having both a force-displacement curve and an associated time-correlated stream of TEM images.

As for force-displacement curve 282 of FIG. 12B, it corresponds to a different aluminum nanograin, yet is similar to force-displacement curve 280 of FIG. 12A in terms of overall characteristics. However, force-displacement curve 282 of FIG. 12B is obviously an improvement over force-displacement curve 282 of FIG. 12A in terms of transducer control performance. For example, the discrete load drops are more crisp in curve 282 of FIG. 12B. Unfortunately, the lack of a displacement sensor dedicated to measuring the extension or the contraction of z segment 188 of 3D piezoelectric actuator 182 deems force-displacement curve 282 of FIG. 12B not fully quantitative, although 3D piezoelectric actuator 182 is found to behave more ideally in high vacuum than in air.

Figure 13A:
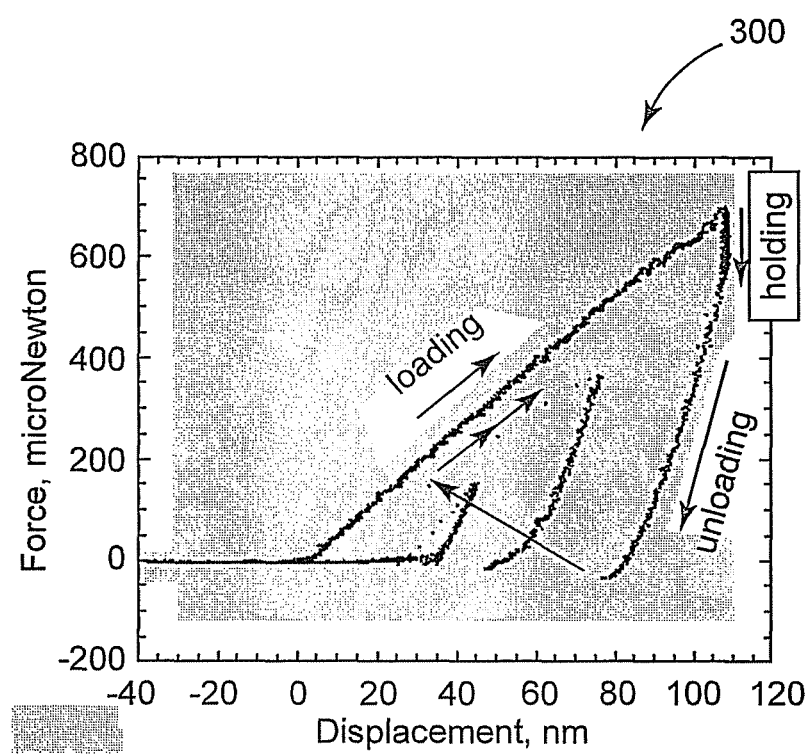
FIG. 13 is a set of quantitative in-situ TEM nanoindentation data for single-crystal silicon obtained with a built actuatable capacitive transducer operating in a JEOL JEM 3010 TEM: a) force-displacement curve while using the displacement control mode; and b) post-test TEM image and electron diffraction patterns.

The following is a second example of quantitative in-situ TEM nanoindentation results that demonstrate the quantitative in-situ TEM nanoindenter's capability of investigating fundamental aspects of nanoscale material deformation. FIG. 13A provides a force-displacement curve 300 corresponding to the same conductive indenter 62 indenting an initially dislocation-free section of the plateau of a wedge-shaped, single-crystal silicon sample not having a film. This nanoindentation test was run in the displacement control mode, and involved a loading segment at a constant displacement rate, followed by a holding segment at a constant penetration depth, followed by an unloading segment at a constant displacement rate. The corresponding time-correlated stream of TEM images indicated an initial period of elastic contact followed by continuous dislocation activity during the remainder of the loading segment, but in contrast to the aluminum nanograins, load drops were not observed.

During the holding segment, stress relaxation gradually occurred even though both the contact area and the nanoindentation-induced dislocation structure seemed to be static. Nothing noteworthy occurred during the unloading segment until experiencing a strong attractive adhesive force (35 µN in magnitude) during the final act of withdrawing the conductive indenter from the sample. At this point, conductive indenter 62 was kicked out suddenly from the sample which forced the control loop to fight back to recover the proper value of displacement in time. This kick-out event is indicated in FIG. 13a by the sequence of arrows. Finally, one more kick-out event occurred before completing the unloading segment, again starting from an attractive adhesive force. The corresponding time-correlated stream of TEM images confirmed the kick-out events being rather violent in nature.

Figure 13B:
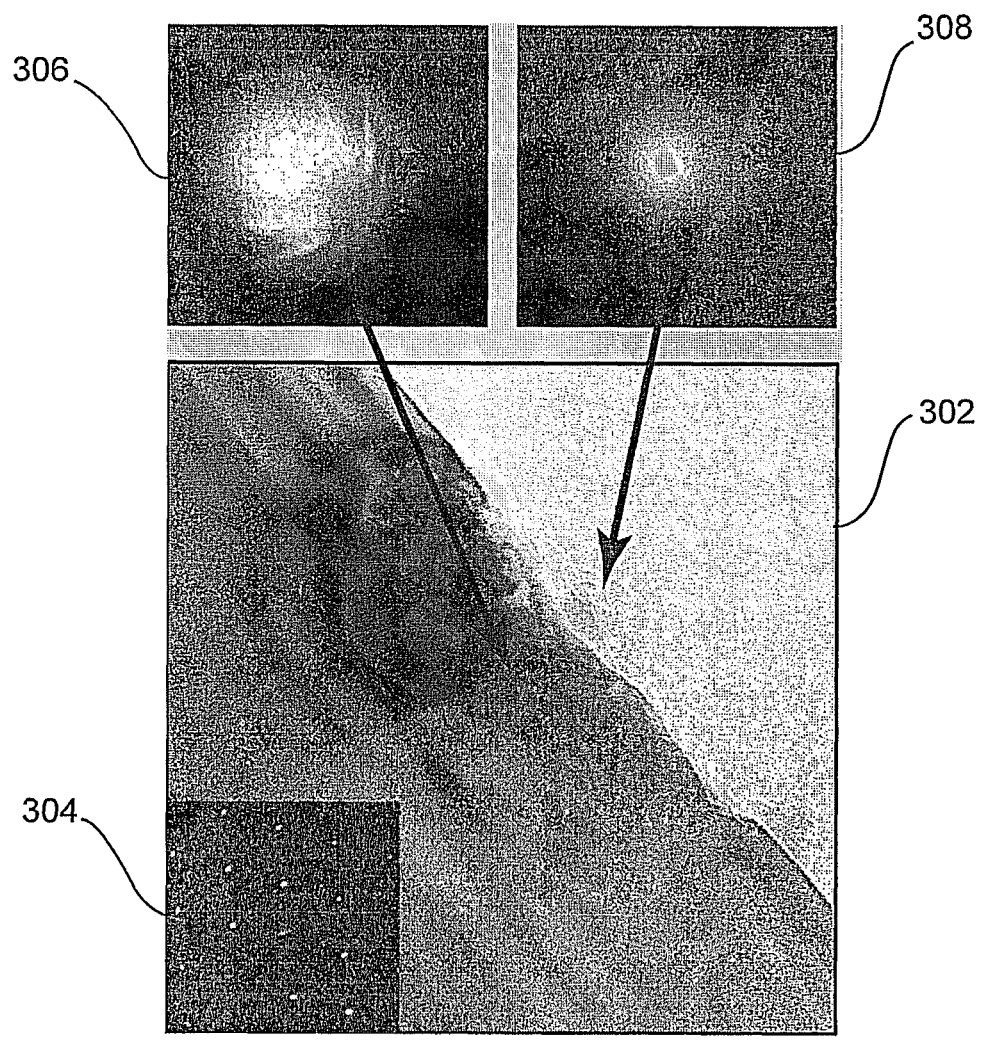

FIG. 13B provides a post-mortem TEM image 302 of the residual deformation zone as well as three post-mortem electron diffraction patterns. Diffraction pattern 304 in the lower left hand corner corresponds to the diamond cubic crystal structure of pristine silicon, nanobeam diffraction pattern 306 in the upper left hand corner also corresponds to the diamond cubic crystal structure but comes from the heavily dislocated region of the residual deformation zone, and nanobeam diffraction pattern 308 of amorphous character in the upper right hand corner comes from the surface pile not present before the nanoindentation test. Apparently, tensile stresses associated with adhesive forces were enough to trigger sudden volume-expanding phase transformations from plastically-deformed, diamond-cubic silicon to amorphous silicon. This particular experimental result raises the interesting possibility of a method that entails viewing/recording the evolution of the nanobeam diffraction pattern throughout the nanoindentation test in order to monitor the local crystal structure as a function of the force-displacement curve.

The following concludes the description of the in-TEM performance results:

1. Actuatable capacitive transducer 30 was stable against the snap-to-contact instability over the software-permitted displacement range of 5 µm.
2. Actuatable capacitive transducer 30 was stable against the spark-gap instability over the range of electric field strength needed to conduct the tests.
3. Corona discharge was not observed. Neither actuatable capacitive transducer 30 nor 3D piezoelectric actuator 182 (also a high voltage device) received power until achieving high vacuum.
4. TEM images did not provide evidence for conductive indenter 62 charging up even when an electrical path from conductive indenter 62 to TEM holder 200 was not provided. This observation suggests force-displacement curves are more sensitive to charging than TEM images.

5. In general, the quantitative in-situ TEM nanoindenter did not exhibit positional drifts large enough to be detected at the magnifications necessary for the tests. Drifting relative to the TEM image's field of view can be ascertained by directly observing the position of conductive indenter 62 and the position of the sample during periods of idle.

6. Although a value for the load frame stiffness was not determined, nothing indicated a load frame stiffness problem.

7. Pumping down the fully-assembled TEM holder after plasma cleaning took approximately 1 hour. In comparison, pumping down the TEM holder 200 prior to receiving the assembly comprised of the internal tube 206, 3D piezoelectric actuator 182, and actuatable capacitive transducer 30 took only about 5 minutes. Although a pump-down time of approximately 1 hour is not intolerable, adding vents to the internal tube should result in an improvement.

8. It is not trivial to properly position conductive indenter 62 with respect to a wedge-shaped sample's plateau because the electron beam transmits through the sample and conductive indenter 62 regardless of whether conductive indenter 62 or the sample is in the foreground relative to the other. A scanning probe microscopy method of imaging in the manner of an AFM but using the indenter rather than a tip on a cantilever, to image the topography of the plateau and the transitions to the sample's side slopes, would be advantageous because such an image could be used as a guide for refining the position of conductive indenter 62 with respect to the plateau, although the process of imaging might damage the sample. In the event of sample damage, the three-dimensional topography image could be used to predict how much to offset 3D piezoelectric actuator 182 in all three spatial dimensions to properly position conductive indenter 62 with respect to a nearby undamaged section of the plateau without contacting the sample. Post-test imaging in the manner of an AFM also enables highly complementary three-dimensional and plan-view images of the residual deformation zone. Imaging in the manner of an AFM could be based on feedback involving z segment 188 of 3D piezoelectric actuator 182 to maintain either a constant spring force if actuatable capacitive transducer 30 is passive during imaging or a constant transducer control effort if actuatable capacitive transducer 30 is active during imaging. The former involves a single feedback loop, whereas the latter involves one feedback loop nested in another, the transducer control loop being the nested loop.

The following begins a description of several embodiments of the present invention. In a preferred embodiment of actuatable capacitive transducer 30, electrostatic actuator 34 rather than the capacitive displacement sensor 36 is closest to conductive indenter 62. In an alternative embodiment of actuatable capacitive transducer 30, capacitive displacement sensor 36 rather than electrostatic actuator 34 is closest to conductive indenter 62. An advantage of electrostatic actuator 34 being closest to conductive indenter 62 is that such an arrangement effectively shortens a length of coupling shaft 46 which is potentially under high load. However, it has been determined that force-displacement curves do not noticeably depend on whether electrostatic actuator 34 or capacitive displacement sensor 36 is closest to conductive indenter 62.

In the preferred embodiment of actuatable capacitive transducer 30, having both first and second multi-plate capacitors 34 and 36 functioning as capacitive displacement sensors might seem redundant at first glance. The reason for electrostatic actuator 34 also functioning as a capacitive displacement sensor has been explained, but not the reason for having a multi-plate capacitor functioning solely as a capacitive displacement sensor. Prior-art actuatable capacitive transducers have been used to conduct dynamic forms of nanoindentation testing as well as dynamic forms of imaging in the manner of an AFM (see References 37-39). However, it is difficult to suppress an oscillatory electrostatic actuation voltage from feeding through, i.e., a portion of the oscillatory electrostatic actuation voltage will appear in the displacement signal if the displacement signal originates from the multi-plate capacitor experiencing the oscillatory electrostatic actuation voltage. This undesirable dynamic feedthrough effect increases in severity with increasing oscillation frequency. Hence, a multi-plate capacitor functioning solely as a capacitive displacement sensor provides means for obtaining a displacement signal free of dynamic feedthrough. This explanation leads to another alternative embodiment of actuatable capacitive transducer 30, wherein one multi-plate capacitor functions solely as a capacitive displacement sensor and another multi-plate capacitor functions solely as an electrostatic actuator, if one is willing to forego the double-sided force-feedback control mode.

Yet another alternative embodiment of actuatable capacitive transducer 30 involves both first and second multi-plate capacitors 34 and 36 functioning as electrostatic actuators to increase the load capacity, and at least one of first and second multi-plate capacitors 34 and 36 functioning as a capacitive displacement sensor, if one is willing to forego dynamic forms of nanoindentation testing/imaging not corrupted by dynamic feedthrough. Of course, it is also feasible to incorporate more than two multi-plate capacitors into actuatable capacitive transducer 30 to yield many possible combinations of multi-plate capacitors functioning as electrostatic actuators and capacitive displacement sensors. Any capacitor being used solely as an electrostatic actuator can be a two-plate capacitor rather than a three-plate type of a multi-plate capacitor.

In the preferred embodiment of actuatable capacitive transducer 30, conductive threaded rod 48 is utilized to electrically connect conductive probe 60 to the remainder of the electrical path responsible for bleeding charge from conductive indenter 62. It is possible to eliminate the need for conductive threaded rod 48 being integral to the electrical path if the probe wire 262 is electrically connected to conductive probe 60 instead, but this is a far more cumbersome solution than the one implemented. Nevertheless, attaching a probe wire to conductive probe 60 is within the scope of the present invention. Eliminating the capacitive displacement sensing function of electrostatic actuator 34 would allow displaceable electrode 42 of electrostatic actuator 34 to be grounded. Conductive threaded rod 48 in electrical contact with the grounded displaceable electrode would prevent conductive indenter 62 from charging up. However, in the case of the JEOL JEM 3010 TEM, this would require sample clamp 212, being electrically isolated from TEM holder 200, to be grounded as well and to avoid sounding the TEM's alarm in the event the electrical conductivity of the indenter-sample contact increased sufficiently. Furthermore, electron beam current passing through displaceable electrode 42 of electrostatic actuator 34 might cause enough noise to be evident in force-displacement curves. Electrically isolating sample clamp 212 from TEM holder 200 does raise the interesting possibility of electrically biasing the sample relative to conductive indenter 62 to measure the electrical conductivity of the indenter-sample contact. But this would be problematic if conductive indenter 62 was electrically connected to displaceable electrode 42 of electrostatic actuator 34 because then displaceable electrode 42 would be increasingly shorted to the sample bias as the electrical conductivity of the indenter-sample contact increased.

Other feasible but non-exhaustive modifications to embodiments of the present invention described herein include significantly shortening the portion of coupling shaft 46 external to conductive transducer body 32, pairing each spring of springs 44 with a mirror image spring, adding a lock-in amplifier to control system 220, and motorizing coarse positioning screws 210. In one scenario, the preferred embodiment of actuatable capacitive transducer 30 could be used for horizontal applications outside a TEM, but it would not be suitable for vertical applications on account of gravity's effect on the relatively high sprung mass. Significantly shortening coupling shaft 46 to sufficiently reduce the sprung mass would allow actuatable capacitive transducer 30 to be used in vertical applications, although this likely would render actuatable capacitive transducer 30 useless in a TEM. Pairing each spring of springs 44 with a mirror image spring would eliminate any tendency of displaceable electrodes 42 to rotate while being displaced, but these additional springs would complicate achieving a relatively low overall spring constant. Adding a lock-in amplifier to control system 220 to measure the amplitude and the phase shift of the oscillatory component of the displacement signal of capacitive displacement sensor 36 during dynamic excitation would facilitate dynamic forms of nanoindentation testing/imaging. Motorizing coarse positioning screws 210 would eliminate the large transients caused by the action of the hand turning the screws, and would enable motor-assisted hunting of the sample's surface in the manner of an AFM. This concludes the description of several embodiments of the invention in addition to the preferred embodiment.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method of quantitative nanoindentation combined with transmission electron microscopy comprising:
    indenting a sample by actuating an actuatable capacitive transducer, wherein actuating includes adjusting voltages supplied to the actuatable capacitive transducer;
    bleeding electrical charge from an electrically conductive indenter of the actuatable capacitive transducer, the charge resulting from an electron beam impinging the electrically conductive indenter, via an electrically conductive path in electrical communication with the electrically conductive indenter, the electrically conductive indenter and electrically conductive path being electrically isolated from other components of the actuatable capacitive transducer;
    recording signals required to generate a representation of a force-displacement relationship; and
    recording a stream of transmission electron microscopy images illustrating one or more aspects of indenting the sample.

2. The method of claim 1, wherein the representation of a force-displacement relationship comprises a force-displacement curve.

3. The method of claim 2, wherein the force-displacement curve comprises a contact force versus a penetration depth curve.

4. The method of claim 1, further comprising recording a time while indenting the sample to generate a representation of a force-time relationship.

5. The method of claim 4, wherein the representation of a force-time relationship comprises a contact force versus time curve.

6. The method of claim 1, further comprising recording a time while indenting the sample to generate a representation of a displacement-time relationship.

7. The method of claim 6, wherein the representation of a displacement-time relationship comprises a penetration depth versus time curve.

8. A method of quantitative nanoindentation combined with transmission electron microscopy comprising:
    indenting a sample by actuating an actuatable capacitive transducer;
    bleeding electrical charge from an electrically conductive indenter, via an electrically conductive path in electrical communication with the electrically conductive indenter, the electrically conductive indenter and electrically conductive path being electrically isolated from other components of the actuatable capacitive transducer;
    controlling a displacement resulting from actuating the actuatable capacitive transducer;
    recording signals required to generate a force-displacement curve; and
    recording a stream of transmission electron microscopy images illustrating one or more aspects of indenting the sample.

9. The method of claim 8, wherein the force-displacement curve comprises a contact force versus a penetration depth curve.

10. The method of claim 8, wherein controlling the displacement involves feedback means and optionally feedforward means.

11. The method of claim 8, further comprising recording a time while indenting the sample to generate a force-time curve and/or a displacement-time curve.

12. A method of quantitative nanoindentation combined with transmission electron microscopy comprising:
    indenting a sample by actuating an actuatable capacitive transducer;
    bleeding electrical charge from an electrically conductive indenter of the actuatable capacitive transducer, via an electrically conductive path in electrical communication with the electrically conductive indenter, the electrically conductive indenter and electrically conductive path being electrically isolated from other components of the actuatable capacitive transducer;
    controlling a contact force resulting from indenting the sample;
    recording signals required to generate a curve representative of the contact force versus a penetration depth; and
    recording a stream of transmission electron microscopy images illustrating one or more aspects of indenting the sample.

13. The method of claim 12, wherein controlling the contact force involves feedback means and optionally feedforward means.

14. The method of claim 12, further comprising recording a time while indenting the sample to generate a curve representative of the contact force versus the time and/or a curve representative of the penetration depth versus the time.

15. A method of quantitative nanoindentation combined with transmission electron microscopy comprising:
   indenting a sample by actuating a piezoelectric actuator while operating an actuatable capacitive transducer in a single-sided force-feedback control mode;
   bleeding electrical charge from an electrically conductive indenter of the actuatable capacitive transducer, via an electrically conductive path in electrical communication with the electrically conductive indenter, the electrically conductive indenter and electrically conductive path being electrically isolated from other components of the actuatable capacitive transducer;
   recording signals required to generate a contact force versus penetration depth curve; and
   recording a stream of transmission electron microscopy images illustrating one or more aspects of indenting the sample.

16. The method of claim 15, further comprising recording a time while indenting the sample to generate a contact force-time curve and/or a penetration depth-time curve.

17. The method of claim 15, wherein operating the actuatable capacitive transducer in the single-sided force-feedback control mode generally prevents a displaceable electrode of the actuatable capacitive transducer from displacing relative to a transducer body of the actuatable capacitive transducer.

18. A method of quantitative nanoindentation combined with transmission electron microscopy comprising:
   indenting a sample by actuating a piezoelectric actuator while operating an actuatable capacitive transducer in a double-sided force-feedback control mode;
   recording signals required to generate a force-feedback curve;
   recording a stream of transmission electron microscopy images illustrating one or more aspects of indenting the sample, wherein operating the actuatable capacitive transducer in the double-sided force-feedback control mode generally prevents a displaceable electrode of the actuatable capacitive transducer from displacing relative to a transducer body of the actuatable capacitive transducer and wherein recording signals includes recording a feedback voltage ideally proportional to a contact force.

19. The method of claim 18, further comprising recording a time while indenting the sample to generate a force-time curve and/or a displacement-time curve.

20. A method of quantitative nanoindentation combined with transmission electron microscopy comprising:
   indenting a sample by actuating an actuatable capacitive transducer;
   controlling a contact force resulting from indenting the sample whenever the contact force is above a specified contact force and controlling a displacement resulting from actuating the actuatable capacitive transducer whenever the contact force is below the specified contact force;
   recording signals required to generate a contact force versus penetration depth curve; and
   recording a stream of transmission electron microscopy images illustrating one or more aspects of indenting the sample.

21. The method of claim 20, further comprising recording a time while indenting the sample to generate a contact force versus time curve and/or a penetration depth versus time curve.

22. The method of claim 20, wherein controlling the contact force and/or controlling the displacement involves feedback means and optionally feedforward means.

23. A method of quantitative nanoindentation combined with transmission electron microscopy comprising:
   indenting a sample;
   bleeding electrical charge form an electrically conductive indenter, via an electrically conductive path in electrical communication with the electrically conductive indenter, the electrically conductive indenter and electrically conductive path being electrically isolated from other components including an actuatable capacitive transducer;
   recording signals required to generate a contact force versus a penetration depth curve; and
   recording a stream of electron diffraction patterns illustrating one or more aspects of indenting the sample.

24. The method of claim 23, further comprising recording a time while indenting the sample to generate a contact force versus time curve and/or a penetration depth versus time curve.

25. A method of positioning an indenter relative to a substantially wedge-shaped sample having a plateau, a first inclined sidewall, and a second inclined sidewall, the method comprising:
   using the indenter to generate a scanning probe microscopy topography image illustrating a portion of the plateau, a portion of the first inclined sidewall, and a portion of the second inclined sidewall;
   determining a three-dimensional spatial orientation of the plateau from the image;
   determining a width of the plateau from the image; and
   positioning the indenter relative to the plateau using the width of the plateau and the three-dimensional spatial orientation of the plateau as a guide.

26. The method of claim 25, wherein positioning the indenter relative to the plateau places the indenter in close proximity to or in contact with the plateau at a location illustrated in the image.

27. The method of claim 25, wherein positioning the indenter relative to the plateau places the indenter in close proximity to or in contact with the plateau at a location not illustrated in the image.

* * * * *